US011177021B2

(12) United States Patent
Chen et al.

(10) Patent No.: US 11,177,021 B2
(45) Date of Patent: Nov. 16, 2021

(54) APPARATUS AND COMPUTERIZED METHOD FOR PREDICTING ASPHALTENE PRECIPITATION BASED ON AGGREGATION THERMODYNAMICS

(71) Applicant: Texas Tech University System, Lubbock, TX (US)

(72) Inventors: Chau-Chyun Chen, Lubbock, TX (US); Yifan Hao, Lubbock, TX (US); Meng Wang, Lubbock, TX (US); Md Rashedul Islam, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 375 days.

(21) Appl. No.: 15/569,233

(22) PCT Filed: Apr. 27, 2016

(86) PCT No.: PCT/US2016/029539
§ 371 (c)(1),
(2) Date: Oct. 25, 2017

(87) PCT Pub. No.: WO2016/176313
PCT Pub. Date: Nov. 3, 2016

(65) Prior Publication Data
US 2018/0314806 A1    Nov. 1, 2018

Related U.S. Application Data

(60) Provisional application No. 62/153,280, filed on Apr. 27, 2015.

(51) Int. Cl.
*G16C 20/30*      (2019.01)
*C09K 8/524*      (2006.01)
(Continued)

(52) U.S. Cl.
CPC .............. *G16C 20/30* (2019.02); *C09K 8/524* (2013.01); *E21B 37/06* (2013.01); *G01N 33/2823* (2013.01)

(58) Field of Classification Search
CPC ...................................... G16C 20/30
See application file for complete search history.

(56) References Cited

U.S. PATENT DOCUMENTS

| 8,346,525 B2 * | 1/2013 | Chen ...................... G16C 20/30 703/12 |
| 2008/0076187 A1 * | 3/2008 | Chen ...................... G16C 20/30 436/161 |

(Continued)

OTHER PUBLICATIONS

Abrams, D.S., et al. "Statistical thermodynamics of liquid mixtures: a new expression for the excess Gibbs energy of partly or completely miscible systems." AIChE Journal. (1975), 21:116-128.

(Continued)

*Primary Examiner* — Hyun D Park
(74) *Attorney, Agent, or Firm* — Edwin S. Flores; Daniel J. Chalker; Chalker Flores, LLP

(57) ABSTRACT

The present invention includes a method for thermodynamic modeling of asphaltene precipitation comprising: calculating the Gibbs free energy for the transition between asphaltene molecules in solution into an imaginary crystalline asphaltene nanoaggregates or asphaltene nanocrystals; calculating the Gibbs free energy for the transition between asphaltene nanoaggregates or nanocrystals redissolving into colloidal asphaltene nanoaggregates using the computer: and predicting asphaltene solubility in a solvent, wherein the predicted asphaltene solubility is used to add a solvent to a liquid, semi-solid, or solid comprising asphaltenes to prevent, e.g., fouling of a wellbore, pipeline, downstream unit operations, to provide flow assurance for crude oil pipeline network, or for petroleum crude blending.

17 Claims, 6 Drawing Sheets

(51) Int. Cl.
*G01N 33/28* (2006.01)
*E21B 37/06* (2006.01)

(56) References Cited

U.S. PATENT DOCUMENTS

| | | | | |
|---|---|---|---|---|
| 2011/0246143 | A1* | 10/2011 | Pomerantz | E21B 49/00 703/2 |
| 2015/0006084 | A1 | 1/2015 | Zuo et al. | |
| 2015/0211357 | A1* | 7/2015 | Chen | E21B 47/06 73/152.27 |

OTHER PUBLICATIONS

Adams, J.J. "Asphaltene adsorption, a literature review." Energy & Fuels. (2014), 28:2831-2856.
Akbarzadeh, K., et al. "A generalized regular solution model for asphaltene precipitation from n-alkane diluted heavy oils and bitumens." Fluid Phase Equilibria. (2005), 232:159-170.
Alboudwarej, H., et al. "Regular solution model for asphaltene precipitation from bitumens and solvents." AIChE Journal. (2003), 49:2948-2956.
Aske, N., et al. "Determination of saturate, aromatic, resin, and asphaltenic (SARA) components in crude oils by means of infrared and near-infrared spectroscopy." Energy & Fuels. (2001), 15:1304-1312.
Bondi, A. Physical properties of molecular crystals, liquids and glasses. New York: John Wiley & Sons, Inc. 1968.
Buckley, J.S. "Microscopic investigation of the onset of asphaltene precipitation." Fuel Science and Technology International. (1996), 14:55-74.
Chapman, W.G., et al. "SAFT: equation-of-state solution model for associating fluids." Fluid Phase Equilibria. (1989), 52:31-38.
Fredenslund, A., et al. "Group-contribution estimation of activity coefficients in nonideal liquid mixtures." AIChE Journal. (1975), 21:1086-1099.
Gómez-Álvarez, P., et al. "Association effects in pure methanol via Monte Carlo simulations. I. structure." Journal of Chemical Physics (2013), 138:44509-44513.
Goual, L., et al. "Cluster of asphaltene nanoaggregates by DC conductivity and centrifugation." Energy & Fuels. (2014), 28:5002-5013.
Goual, L., et al. "On the formation and properties of asphaltene nanoaggregates and clusters by DC-conductivity and centrifugation." Fuel. (2011), 90:2480-2490.
Gross, J., et al. "Perturbed-chain SAFT: an equation of state based on a perturbation theory for chain molecules." Industrial & Engineering Chemistry Research. (2001), 40:1244-1260.
Hansen, H.K., et al. "Vapor-liquid equilibria by UNIFAC group contribution. 5. revision and extension." Industrial & Engineering Chemistry Research. (1991), 30:2352-2355.
Hermida-Ramón, J.M., et al. "The energy of interaction between two acetone molecules: a potential function constructed from ab Initio data." The Journal of Physical Chemistry A. (1998), 102:2594-2602.
International Search Report and Written Opinion—PCT/US2016/029539 [AU/RO] dated Jul. 20, 2016.

Mannistu, K.D., et al. "Solubility modeling of asphaltenes in organic solvents." Energy & Fuels. (1997), 11:615-622.
Mullins, O.C. "The modified Yen model." Energy & Fuels. (2010), 24:2179-2207.
Mullins, O.C., et al. "Advances in asphaltene science and the Yen-Mullins model." Energy & Fuels. (2012), 26:3986-4003.
Mullins, O.C., et al. "Clusters of asphaltene nanoaggregates observed in oilfield reservoirs." Energy & Fuels. (2013), 27:1752-1761.
Nikooyeh, K., et al. "On the applicability of the regular solution theory to asphaltene + diluent mixtures." Energy & Fuels. (2012), 26:576-585.
Oh, K., et al. "Asphaltene aggregation in organic solvents. Journal of Colloid and Interface Science." (2004), 271:212-219.
Rane, J.P., et al. "Adsorption kinetics of asphaltenes at the oil-water interface and nanoaggregation in the bulk." Langmuir. (2012), 28:9986-9995.
Rane, J.P., et al. "Interfacial rheology of asphaltenes at oil-water interfaces and interpretation of the equation of state." Langmuir. (2013), 29:4750-4759.
Rassamdana, H., et al. "Asphalt flocculation and deposition: I. the onset of precipitation." AIChE Journal. (1996), 42:10-22.
Sayegh, S.G., et al. "Lattice-model expressions for the combinatotial entropy of liquid mixtures: a critical discussion." The Chemical Engineering Journal. (1980), 19:1-10.
Schuler, B., et al. "Unraveling the molecular structures of asphaltenes by atomic force microscopy." Journal of the American Chemical Society. (2015), 137:9870-9876.
Sheu, E.Y. "Petroleum asphaltene properties, characterization, and issues. Energy & Fuels." (2002), 16:74-82.
Tanveer, S., et al. "Introduction to solid-fluid equilibrium modeling." Chemical Engineering Progress. (2014), 110:37-47.
Tharanivasan, A.K., et al. "Application of a regular solution-based model to asphaltene precipitation from live oils." Energy & Fuels. (2011), 25:528-538.
Tharanivasan, A.K., et al. "Measurement and modeling of asphaltene precipitation from crude oil blends." Energy & Fuels. (2009), 23:3971-3980.
Vargas, F.M., et al. "Modeling asphaltene phase behavior in crude oil systems using the perturbed chain form of the statistical associating fluid theory (PC-SAFT) equation of state." Energy & Fuels. (2009), 23:1140-1146.
Victorov, A.I., et al. "Thermodynamic micellizatin model of asphaltene precipitation from petroleum fluids." AIChE Journal. (1996), 42:1753-1764.
Wiehe, I.A., et al. The paradox of asphaltene precipitation with normal paraffins. Energy & Fuels. (2005), 19:1261-1267.
Wu, J., et al. "Molecular thermodynamics of asphaltene precipitation in reservoir fluids." AIChE Journal. (2000), 46:197-209.
Wu, J., et al. "Molecular-thermodynamic framework for asphaltene-oil equilibria." AIChE Journal. (1998), 44:1188-1199.
Yoon, S., et al. "Separation and characterization of bitumen from Athabasca oil sand." Korean J. Chem. Eng. (2009), 26:64-71.
Zanganeh, P., et al. "Asphaltene deposition during CO2 injection and pressure depletion: a visual study." Energy & Fuels. (2012), 26:1412-1419.
Zuo, J.Y., et al. Advances in the Flory-Huggins-Zuo equation of state for asphaltene gradients and formation evaluation. Energy & Fuels. (2013), 27:1722-1735.

\* cited by examiner

Prior Art

Prior Art

Prior Art

APPARATUS AND COMPUTERIZED METHOD FOR PREDICTING ASPHALTENE PRECIPITATION BASED ON AGGREGATION THERMODYNAMICS

CROSS-REFERENCE TO RELATED APPLICATIONS

This application claims priority to, and is the National Phase of International Application No. PCT/US2016/029539, filed on Apr. 27, 2016, which claims the benefit under 35 U.S.C. § 119(e) of U.S. Provisional Application No. 62/153,280, filed Apr. 27, 2015. All of which are hereby incorporated by reference in their entirety.

TECHNICAL FIELD OF THE INVENTION

The present invention relates in general to the field of computer modeling, and more particularly, to a novel method for the prediction of asphaltene precipitation based on aggregation thermodynamics.

BACKGROUND OF THE INVENTION

Without limiting the scope of the invention, its background is described in connection with in silico chemical predictions.

A priori prediction of fluid phase equilibria and liquid phase non-idealities has played a key role in modern chemical process and product development. A number of successful excess Gibbs energy models have been developed that can describe phase behavior a priori with either qualitative or semi-quantitative accuracy. Examples include group contribution method, i.e., Universal Quasi-Chemical Functional-Group Activity Coefficients (UNIFAC), conceptual segment approach, i.e., Non-Random Two-Liquid Segment Activity Coefficients (NRTL-SAC), and solvation thermodynamics approach, i.e. Conductor Like Screening Model for Real Solvents (COSMO-RS) and Conductor Like Screening Model for Segment Activity Coefficients (COSMO-SAC).

Group contribution method is one of the early ideas for the prediction models. Among the group contribution methods, UNIFAC is the most accurate and widely used. UNIFAC defines chemical compounds and their mixtures in terms of tens of predefined chemical functional groups. Interaction parameters that accounts for inter-molecular interactions between different functional groups are first optimized from millions of available experimental phase equilibrium data for molecules with the predefined functional groups. They are then employed to predict liquid phase non-idealities, i.e., activity coefficients, of molecules in mixtures with the predefined functional groups. In contrast, NRTL-SAC defines four conceptual segments each uniquely representing functional groups or molecular fragments exhibiting hydrophobic, polar attractive, polar repulsive, or hydrophilic nature in molecular interactions. Interaction parameters for the four conceptual segments are identified from selected reference solvents and real molecules that exhibit hydrophobicity, solvation, polarity, and hydrophilicity. Activity coefficients of compounds in mixtures can then be predicted with NRTL-SAC as long as all of the compounds in the mixture have been characterized with their equivalent conceptual segment numbers for hydrophobicity, solvation, polarity, and hydrophilicity.

Solvation-thermodynamics predicts thermo-physical properties based on charge distribution over molecular surface. Among the solvation-thermodynamics based models, COSMO is the most widely used. There are two different variants of COSMO, i.e. COSMO-RS and COSMO-SAC. Unlike UNIFAC and NRTL-SAC, this method determines the interaction between molecules based on so called sigma profiles, i.e., a histogram of charge density distribution over the molecular surface based on molecular structure and quantum mechanical computations. Used together with a statistical thermodynamic expression, the resultant charge density distributions compute chemical potentials of molecules in solution. The solvation thermodynamic models are advantageous over UNIFAC and NRTL-SAC when experimental data are very limited or even no experimental data is available. However COSMO requires knowledge of molecular structure to generate sigma profiles and the prediction quality of COSMO is qualitative and often considered less reliable than UNIFAC and NRTL-SAC.

SUMMARY OF THE INVENTION

In one embodiment, the present invention includes a computerized method for thermodynamic modeling of asphaltene precipitation comprising: calculating the Gibbs free energy for the transition between asphaltene molecules in solution into an imaginary crystalline asphaltene nanoaggregates or asphaltene nanocrystals using a computer; calculating the Gibbs free energy for the transition between asphaltene nanoaggregates or nanocrystals redissolving into colloidal asphaltene nanoaggregates using the computer; and predicting asphaltene solubility in a solvent, wherein the predicted asphaltene solubility is displayed on an output device communicably coupled to the computer. In one aspect, the step of calculating the transition between asphaltene molecules in solution into an imaginary crystalline asphaltene nanoaggregates or asphaltene nanocrystals is defined further as calculating the transition between

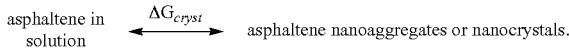

In another aspect, the step of calculating the transition between asphaltene molecules in solution into an imaginary crystalline asphaltene nanoaggregates or asphaltene nanocrystals is defined further as calculating:

$$\Delta G_{cryst} = -\Delta G_{fus} = RT \ln K_{sp} \quad (1)$$

where R is ideal gas constant, T is the system temperature, $\Delta G_{fus}$ is Gibbs free energy of fusion and Ksp is the solubility product constant of the imaginary asphaltene nanocrystals. In another aspect, the step of calculating the transition between asphaltene nanoaggregates or nanocrystals redissolving in to colloidal asphaltene nanoaggregates is defined further as calculating:

$$\Delta G_{colloid} \approx RT \ln \gamma_{nano}^{\infty} \quad (2)$$

where $\gamma_{nano}^{\infty}$ is the "infinite dilution activity coefficient" of the nanoaggregates in solution. In another aspect, the processor calculates the thermodynamic model of solubility of asphaltenes using at least one of Formulas 1 to 22, at least one of Tables 1 to 4, or combinations thereof.

Another embodiment of the present invention includes a method for preventing asphaltene fouling of a wellbore, pipeline, downstream unit operations, to provide flow assurance for crude oil pipeline network, or for petroleum crude blending with a solvent that prevents asphaltene precipitation or that redissolves precipitated asphaltenes based on a predictive thermodynamic model comprising: calculating the Gibbs free energy for the transition between asphaltene molecules in solution into an imaginary crystalline asphaltene nanoaggregates or asphaltene nanocrystals; calculating the Gibbs free energy for the transition between asphaltene nanoaggregates or nanocrystals redissolving into colloidal asphaltene nanoaggregates; predicting asphaltene solubility using different solvents using the predictive thermodynamic model; selecting a solvent based on the predictive thermodynamic model; and calculating an amount of the solvent sufficient to prevent fouling of the wellbore, pipeline, downstream unit operations, to provide flow assurance for crude oil pipeline network, or for petroleum crude blending. In one aspect, the step of calculating the transition between asphaltene molecules in solution into an imaginary crystalline asphaltene nanoaggregates or asphaltene nanocrystals is defined further as calculating the transition between

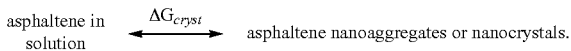

In another aspect, the step of calculating the transition between asphaltene molecules in solution into an imaginary crystalline asphaltene nanoaggregates or asphaltene nanocrystals is defined further as calculating:

$$\Delta G_{cryst} = -\Delta G_{fus} = RT \ln K_{sp} \quad (1)$$

where R is ideal gas constant, T is the system temperature, $\Delta G_{fus}$ is Gibbs free energy of fusion and Ksp is the solubility product constant of the imaginary asphaltene nanocrystals. In another aspect, the step of calculating the transition between asphaltene nanoaggregates or nanocrystals redissolving into colloidal asphaltene nanoaggregates is defined further as calculating:

$$\Delta G_{colloid} \approx RT \ln \gamma_{nano}^{\infty} \quad (2)$$

where $\gamma_{nano}^{\infty}$ is the "infinite dilution activity coefficient" of the nanoaggregates in solution. In another aspect, the step of calculating the thermodynamic model of solubility of asphaltenes uses at least one of Formulas 1 to 22, at least one of Tables 1 to 4, or combinations thereof. In another aspect, the step of calculating an amount of the solvent identified is added to an asphaltene to prevent asphaltene nanoaggregate or asphaltene nanocrystal formation, or that solubilizes asphaltene nanoaggregate or asphaltene nanocrystal into colloidal asphaltene nanoaggregates to prevent fouling of the wellbore, pipeline, downstream unit operations, to provide flow assurance for crude oil pipeline network, or for petroleum crude blending. In another aspect, the method further comprises adding an amount of a solvent to a formation to prevent formation damage and plugging of the well bore, or correcting formation damage and un-plugging of the well bore.

Yet another embodiment is a non-transitory computer readable medium encoded with a computer program for execution by a processor for optimizing a predictive thermodynamic model for asphaltene molecules, the computer program comprising: a code segment for calculating surface interaction characteristics of asphaltene molecules with a solvent using a computer by: calculating the Gibbs free energy for the transition between asphaltene molecules in solution into an imaginary crystalline asphaltene nanoaggregates or asphaltene nanocrystals using a computer; calculating the Gibbs free energy for the transition between asphaltene nanoaggregates or nanocrystals redissolving into colloidal asphaltene nanoaggregates using the computer; and a code segment for predicting asphaltene solubility in the solvent, wherein the predicted asphaltene solubility is displayed on an output device communicably coupled to the computer. In another aspect, the medium further comprises a code segment for calculating the transition between asphaltene molecules in solution into an imaginary crystalline asphaltene nanoaggregates or asphaltene nanocrystals is defined further as calculating the transition between

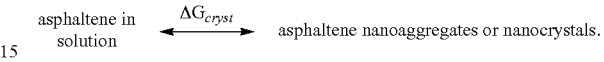

In another aspect, the medium further comprises a code segment for calculating the transition between asphaltene molecules in solution into an imaginary crystalline asphaltene nanoaggregates or asphaltene nanocrystals is defined further as calculating:

$$\Delta G_{cryst} = -\Delta G_{fus} = RT \ln K_{sp} \quad (1)$$

where R is ideal gas constant, T is the system temperature, $\Delta G_{fus}$ is Gibbs free energy of fusion and Ksp is the solubility product constant of the imaginary asphaltene nanocrystals. In another aspect, the medium further comprises a code segment for calculating the transition between asphaltene nanoaggregates or nanocrystals redissolving into colloidal asphaltene nanoaggregates is defined further as calculating:

$$\Delta G_{colloid} \approx RT \ln \gamma_{nano}^{\infty} \quad (2)$$

where $\gamma_{nano}^{\infty}$ is the "infinite dilution activity coefficient" of the nanoaggregates in solution. In another aspect, the processor calculates the thermodynamic model of solubility of asphaltenes using at least one of Formulas 1 to 19, at least one of Tables 1 to 4, or combinations thereof. In another aspect, the processor calculates an amount of the solvent identified that prevents asphaltene nanoaggregate or asphaltene nanocrystal formation, or that solubilizes asphaltene nanoaggregate or asphaltene nanocrystal into colloidal asphaltene nanoaggregates.

Yet another embodiment of the present invention includes an apparatus for optimizing a thermodynamic model of solubility of asphaltenes comprising: a processor; a memory communicably coupled to the processor; an output device communicably coupled to the processor; and a non-transitory computer readable medium encoded with a computer program for execution by the processor that causes the processor to: calculate the Gibbs free energy for the transition between asphaltene molecules in solution into an imaginary crystalline asphaltene nanoaggregates or asphaltene nanocrystals using a computer and to calculate the Gibbs free energy for the transition between asphaltene nanoaggregates or nanocrystals redissolving into colloidal asphaltene nanoaggregates using the computer, wherein the processor outputs solubility data for the asphaltenes in one or more solvents. In one aspect, the processor calculates the transition between asphaltene molecules in solution into an imaginary crystalline asphaltene nanoaggregates or asphaltene nanocrystals is defined further as calculating the transition between

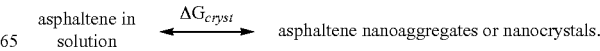

In one aspect, the processor calculates the transition between asphaltene molecules in solution into an imaginary crystalline asphaltene nanoaggregates or asphaltene nanocrystals is defined further as calculating:

$$\Delta G_{cryst} = -\Delta G_{fus} = RT \ln K_{sp} \qquad (1)$$

where R is ideal gas constant, T is the system temperature, $\Delta G_{fus}$ is Gibbs free energy of fusion and Ksp is the solubility product constant of the imaginary asphaltene nanocrystals. In one aspect, the processor calculates the transition between asphaltene nanoaggregates or nanocrystals redissolving into colloidal asphaltene nanoaggregates is defined further as calculating:

$$\Delta G_{colloid} \cong RT \ln \gamma_{nano}^{\infty} \qquad (2)$$

where $\gamma_{nano}^{\infty}$ is the "infinite dilution activity coefficient" of the nanoaggregates in solution. In one aspect, the processor calculates the thermodynamic model of solubility of asphaltenes using at least one of Formulas 1 to 22, at least one of Tables 1 to 4, or combinations thereof. In one aspect, the processor calculates an amount of the solvent identified to be added to an asphaltene comprising liquid or solid that prevents asphaltene nanoaggregate or asphaltene nanocrystal formation, or that solubilizes asphaltene nanoaggregate or asphaltene nanocrystal into colloidal asphaltene nanoaggregates to prevent fouling of the wellbore, pipeline, downstream unit operations, to provide flow assurance for crude oil pipeline network, or for petroleum crude blending.

Yet another embodiment of the present invention includes a non-transitory computer readable medium encoded with a computer program for execution by a processor for generating a thermodynamic model of solubility of asphaltenes, the computer program comprising: calculating the Gibbs free energy for the transition between asphaltene molecules in solution into an imaginary crystalline asphaltene nanoaggregates or asphaltene nanocrystals using a computer; calculating the Gibbs free energy for the transition between asphaltene nanoaggregates or nanocrystals redissolving into colloidal asphaltene nanoaggregates using the computer; and predicting asphaltene solubility using different solvents using the predictive thermodynamic model; selecting a solvent based on the predictive thermodynamic model; and calculating an amount of the solvent sufficient to prevent asphaltene precipitation, or to redissolve precipitated asphaltene, wherein the solvent prevents fouling of the wellbore, the pipeline, the downstream unit operations, provides flow assurance for the crude oil pipeline network, or for petroleum crude blending. In one aspect, the medium further comprises a code segment for calculating the transition between asphaltene molecules in solution into an imaginary crystalline asphaltene nanoaggregates or asphaltene nanocrystals is defined further as calculating the transition between

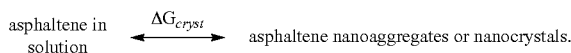

In another aspect, the medium further comprises a code segment for calculating the transition between asphaltene molecules in solution into an imaginary crystalline asphaltene nanoaggregates or asphaltene nanocrystals is defined further as calculating:

$$\Delta G_{cryst} = -\Delta G_{fus} = RT \ln K_{sp} \qquad (1)$$

where R is ideal gas constant, T is the system temperature, $\Delta G_{fus}$ is Gibbs free energy of fusion and Ksp is the solubility product constant of the imaginary asphaltene nanocrystals. In another aspect, the medium further comprises a code segment for calculating the transition between asphaltene nanoaggregates or nanocrystals redissolving into colloidal asphaltene nanoaggregates is defined further as calculating:

$$\Delta G_{colloid} \cong RT \ln \gamma_{nano}^{\infty} \qquad (2)$$

where $\gamma_{nano}^{\infty}$ is the "infinite dilution activity coefficient" of the nanoaggregates in solution. In another aspect, the processor calculates the thermodynamic model of solubility of asphaltenes using at least one of Formulas 1 to 22, at least one of Tables 1 to 4, or combinations thereof. In another aspect, the processor calculates an amount of the solvent identified to be added to an asphaltene comprising liquid or solid that prevents asphaltene nanoaggregate or asphaltene nanocrystal formation, or that solubilizes asphaltene nanoaggregate or asphaltene nanocrystal into colloidal asphaltene nanoaggregates to prevent fouling of the wellbore, pipeline, downstream unit operations, to provide flow assurance for crude oil pipeline network, or for petroleum crude blending.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
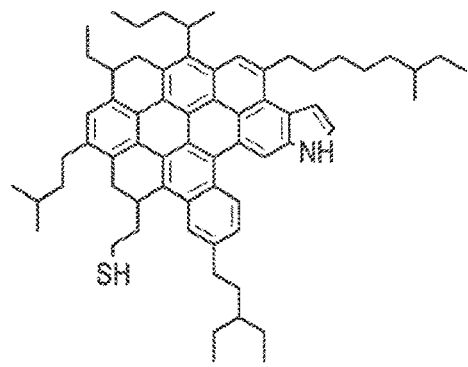
FIGS. 1A-1B show the two-step process for asphaltene aggregation.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Asphaltenes are the heaviest non-distillable fraction of crude oil. The chemical identity of asphaltenes is often obscured. Further, asphaltenes are in a solubility class of components that are insoluble in n-heptane and soluble in toluene.

Generally, the characteristics of asphaltenes are as follows: the presence of asphaltenes strongly affects viscosity, which can lead to plugging pipelines and increase operational cost. When operating at scale, asphaltenes often lead to fouling of unit operations, safety hazards, and decreased production efficiency. Further, asphaltenes alter rock permeability and can cause formation damage and plug the well bore. When processing crude, asphaltenes cause catalyst coking, block catalyst pores, and reduce processing efficiency.

The present invention includes a computer method that predicts asphaltene solubility based on aggregation thermodynamics, activity coefficients for asphaltene in solution, and activity coefficients for nano-aggregates in solution.

Asphaltene precipitation is a major petroleum industry issue and existing prediction methods are largely based on empiricism. Asphaltene precipitation affects flow assurance for crude oil pipeline network and is required for petroleum crude blending.

The invention offers a novel thermodynamic view to asphaltene precipitation and makes it possible to predict asphaltene solubility based on rigorous thermodynamics. The present invention will find particular uses in upstream, midstream, and downstream petroleum processing; engineering and construction; and process simulation of the same.

The present inventors have found that precipitation of asphaltene causes many problems, including: (1) plugging up well bores and pipelines; (2) fouling of unit operations and decreasing production efficiency; and/or (3) poisoning of catalysts, as non-limiting examples. The present invention helps identify the best possible solvents for preventing, e.g., plugging up well bores and pipelines; fouling of unit operations and decreasing production efficiency; and/or poisoning of catalysts during processing of liquids, semi-solids or solids that comprise asphaltenes. The present invention can also be used to determine the solvent and amount of solvent used downhole to prevent formation damage and plugging of the well bore, or in certain circumstances, correcting formation damage and un-plugging of the well bore.

The invention includes a thermodynamic model that uses NRTL-SAC and UNIFAC activity coefficient models to determine the solubility of organic solvents. The new model allows for rapid prediction of the precipitation of Asphaltenes both qualitatively and/or semi-quantitatively. The determination of the asphaltene precipitation point is essential in the petroleum industry because asphaltenes are known to plug up pipelines. Because of the wide rage of molecular weights, it becomes hard to determine when the precipitation of asphaltenes occurs. The present invention is an improved derivative model of NRTL that exploits the interaction characteristics of molecules to improve asphaltene modeling.

Aggregation Thermodynamics for Asphaltene Precipitation.

Asphaltene precipitation has been a major concern for petroleum industry due to its adverse effect upon upstream production, midstream transportation, and downstream refining. As a complex phenomenon involving solubility, aggregation, and clustering, asphaltene precipitation has been extensively investigated and correlated with empirical models and equations. Based on the insight regarding hierarchical structure of asphaltenes recently elucidated by Mullins, the inventors present a thermodynamic formulation for asphaltene aggregation at the onset of asphaltene precipitation. The thermodynamic formulation accounts for asphaltene aggregation driving force as a two-step process: (1) molecular asphaltene forming imaginary "nanocrystals," and (2) "nanocrystals" re-dissolving as colloidal nanoaggregates. Applying the Universal Quasi-Chemical Functional-Group Activity Coefficients (UNIFAC) with this thermodynamic formulation, the inventors show semi-quantitative predictions of asphaltene precipitation in 13 binary solvents with wide varieties of chemical structures and solvent combinations.

This example examines the onset of asphaltene precipitation, and illustrates how the liquid phase affects asphaltene solubility. The onset of precipitation is assumed to be critical nanoaggregate concentration (CNAC), the transition point of asphaltene molecular solution to colloidal solution. Based on the hierarchical structure of asphaltenes proposed by the Yen-Mullins model, the inventors present the so-called aggregation thermodynamics for asphaltene precipitation. This thermodynamic formulation accounts for the driving force for asphaltene aggregation as a two-step process: (1) molecular asphaltene forming imaginary crystalline nanoaggregates, or "nanocrystals", and (2) the "nanocrystals" re-dissolving as colloidal nanoaggregates. To quantify the asphaltene aggregation process, the functional group contribution activity coefficient model UNIFAC[30] is employed for calculating the activity coefficients and the Gibbs free energy changes. The thermodynamic formulation is then validated by comparing the calculated asphaltene solubility with the experimental data of Mannistu et al.[16], who reported 15 sets of asphaltene solubility data in binary solvents with wide varieties of chemical structures and solvent combinations.

Thermodynamic Formulation. The inventors considered the formation of asphaltene nanoaggregates as the starting point of precipitation. From a thermodynamics perspective, the focus is on the driving force for the formation of asphaltene nanoaggregates.

Figure 1B:
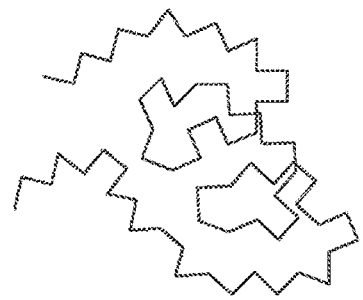

Chemical structure of asphaltenes and asphaltene nanoaggregates. Asphaltene molecules are thousands in number and vary in chemical structure. It is not realistic to describe every possible asphaltene molecule participating in the formation of asphaltene nanoaggregates. Therefore, a representative asphaltene molecular structure, shown in FIG. 1A, is chosen based on the Yen-Mullins model. Characteristic features of asphaltene molecules include central fused aromatic rings and peripheral alkyl substituents. Heteroatoms like sulfur, nitrogen, and oxygen can appear in both the central fused ring and/or the alkyl side chains. To account for the chemical structure of asphaltene nanoaggregates, an even bolder but experimentally supported assumption has been made with the Yen-Mullins model. Accordingly, asphaltene nanoaggregates exist as a "hairy tennis ball" in solvent, suggesting that only the alkyl side chains are exposed to and dissolved in the solvent, and contribute to the interaction between asphaltene nanoaggregates and solvent molecules. Following the Yen-Mullins model, and solely as a means of explanation and in no way a limitation of the present invention, the inventors provide a simple thermodynamic formulation to calculate the driving force for the formation of asphaltene nanoaggregates. The inventors further account for the alkyl side chain-solvent interaction by examining the carbon number of the alkane molecule, shown in FIG. 1B, required to describe the solubility behavior of the nanoaggregates in solvents.

Aggregation thermodynamics. To quantify the Gibbs free energy change of the aggregation process, a two-step process is assumed as follows.

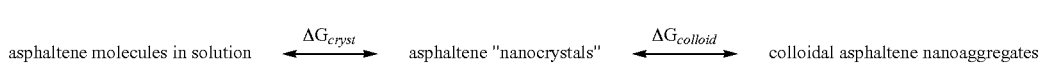

(R1)

Figure 2:
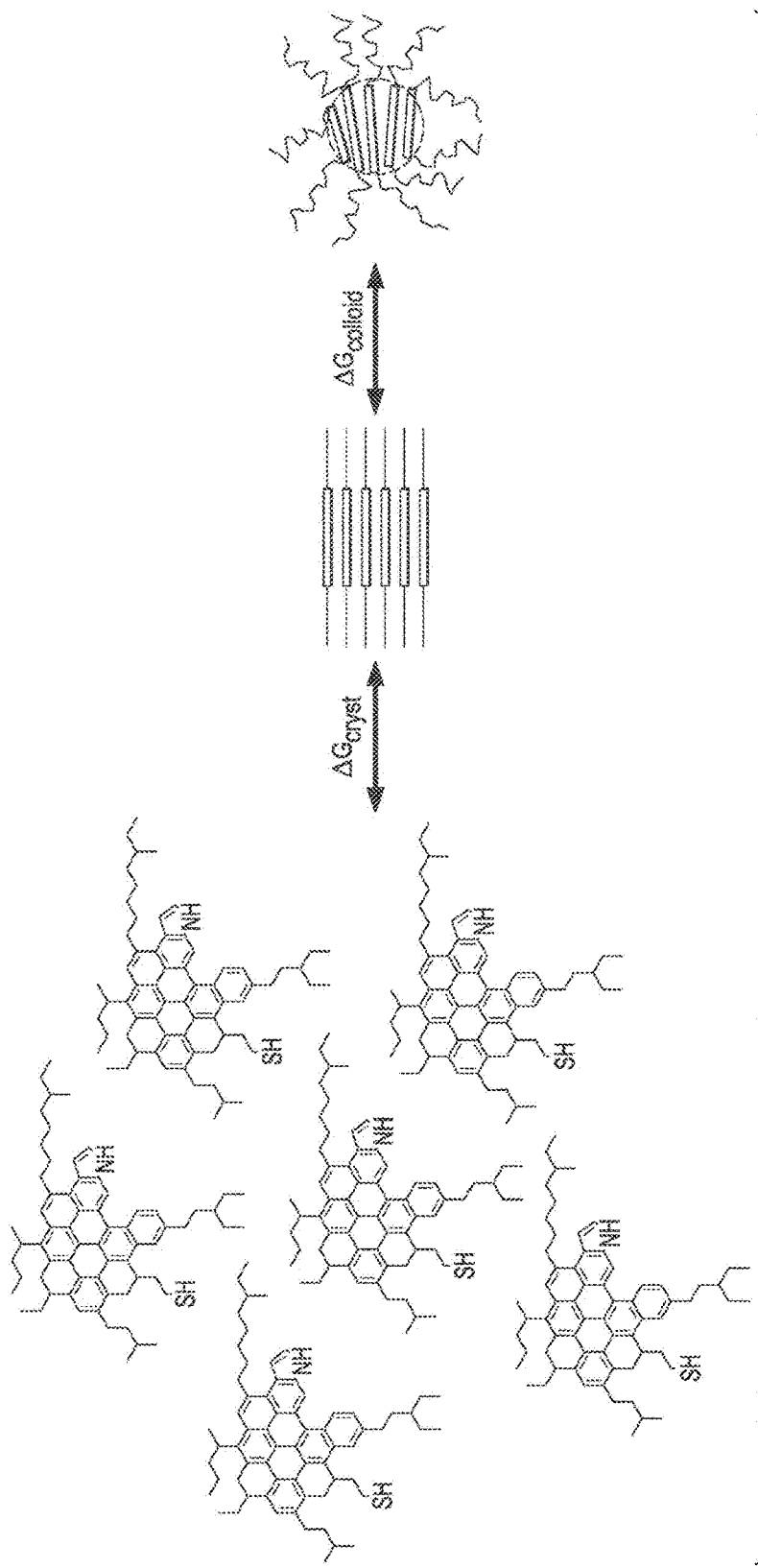
FIG. 2 is a comparison of asphaltene solubility between experimental data (symbols)[16] and "crystallization" model predicted results (lines) in binary solvents of toluene+n-pentane (line of small dashes), n-hexane (line of medium size dashes), n-heptane (line of large dashes), n-octane (line of alternating dashes and dots), and n-decane (solid line)

As shown in FIG. 2, in the first step asphaltene molecules form highly ordered imaginary crystalline nanoaggregates, or "nanocrystals". The change of Gibbs free energy of crystallization, $\Delta G_{cryst}$, can be described in terms of solubility product constant.

$$\Delta G_{cryst} = -\Delta G_{fus} = RT \ln K_{sp} \quad (1)$$

where R is ideal gas constant, T is the system temperature, $\Delta G_{fus}$ is Gibbs free energy of fusion and $K_{sp}$ is the solubility product constant of the imaginary asphaltene "nanocrystals."

In the second step, the imaginary "nanocrystals" "re-dissolve" and form colloidal nanoaggregates with the alkyl side chains exposed to the solvents while the central fused rings remain in crystalline state. At the onset of asphaltene precipitation, the Gibbs free energy change for the "re-dissolving" process should approximately correspond to the "infinite dilution activity coefficient" of the colloidal nanoaggregates in solution.

$$\Delta G_{colloid} \cong RT \ln \gamma_{nano}^{\infty} \quad (2)$$

where $\gamma_{nano}^{\infty}$ is the "infinite dilution activity coefficient" of the nanoaggregates in solution. Since only the alkyl side chains are exposed to the solvent, $\gamma_{nano}^{\infty}$ should be dominated by the interaction between the alkyl side chains and the surrounding solvent molecules. $\gamma_{nano}^{\infty}$ is a function of solvent composition.

Summing up steps 1 and 2, the Gibbs free energy change for the nanoaggregate formation process can be accounted for as follows.

$$\Delta G_{agg} = \Delta G_{cryst} + \Delta G_{colloid} = RT[\ln K_{sp} + \ln \gamma_{nano}^{\infty}] \quad (3)$$

The equivalent solubility product constant for the asphaltene nanoaggregate formation process, $K_{sp}^{agg}$, can be defined from the change of Gibbs free energy:

$$\ln K_{sp}^{agg} = \frac{\Delta G_{agg}}{RT} = \ln x_{asp}^{agg} + \ln \gamma_{asp}^{agg} \quad (4)$$

where $x_{asp}$ and $\gamma_{asp}$ are the mole fraction and the activity coefficient of asphaltene molecule in solution, respectively. Superscript agg stands for asphaltene saturation per the nanoaggregate formation process, or the onset of precipitation.

In summary, to calculate the asphaltene saturation concentration $x_{asp}^{agg}$ at the onset of asphaltene precipitation, the following are used: $K_{sp}$, $\gamma_{asp}^{agg}$, and $\gamma_{nano}^{\infty}$. As shown herein, the UNIFAC model was chosen to predict the activity coefficients.

UNIFAC activity coefficient model. As a group contribution method, the UNIFAC model predicts activity coefficients for molecules in liquid mixtures based on functional groups that make up the molecules. The model is well proven for small organic molecules and widely used in chemical and petrochemical industries.

According to UNIFAC, logarithm of activity coefficient of component i in a mixture is the sum of two parts: a combinatorial part and a residual part.

$$\ln \gamma_i = \ln \gamma_i^C + \ln \gamma_i^R \quad (5)$$

where the combinatorial part is calculated with the lattice model of Staverman and Guggenheim[31].

$$\ln \gamma_i^C = \ln \frac{\Phi_i}{x_i} + \frac{z}{2} q_i \ln \frac{\theta_i}{\Phi_i} + l_i - \frac{\Phi_i}{x_i} \sum_j x_j l_j \quad (6)$$

$$l_i = \frac{z}{2}(r_i - q_i) - (r_i - 1); z = 10 \quad (7)$$

$$\theta_i = \frac{q_i x_i}{\sum_j q_j x_j}; \quad \Phi_i = \frac{r_i x_i}{\sum_j r_j x_j} \quad (8)$$

where $x_i$ is the mole fraction of component i, z is the coordination number, $\theta_i$ is the surface area fraction, and $\Phi_i$ is the segment fraction which is similar to the volume fraction. $r_i$ and $q_i$ are the pure component volume and area parameter, respectively, and calculated by summing up the group volume and area parameters.

$$r_i = \Sigma_k v_k^{(i)} R_k; \quad q_i = \Sigma_k v_k^{(i)} Q_k \quad (9)$$

where $v_k^{(i)}$ is an integer representing the number of type k group in molecule i. Group parameters $R_k$ and $Q_k$ are obtained from the van der Waals group volume and surface area $V_{wk}$ and $A_{wk}$ by Bondi[32].

$$R_k = \frac{V_{wk}}{15.17}; \quad Q_k = A_{wk}/(2.5 \cdot 10^9) \quad (10)$$

where the normalization factors 15.17 cm³/mol and 2.5·10⁹ cm²/mol are given by Abrams and Prausnitz[33].

For the residual part of logarithm of activity coefficient, the solution-of-groups concept is employed.

$$\ln \gamma_i^R = \Sigma_k v_k^{(i)} [\ln \Gamma_k - \ln \Gamma_k^{(i)}] \quad (11)$$

where $\Gamma_k$ is the group residual activity coefficient, and $\Gamma_k^{(i)}$ is the residual activity coefficient of group k in a reference solution containing only molecules of type i.

$$\ln \Gamma_k = Q_k \left[ 1 - \ln\left(\sum_m \Theta_m \Psi_{mk}\right) - \sum_m \left(\frac{\Theta_m \Psi_{km}}{\sum_n \Theta_n \Psi_{nm}}\right) \right] \quad (12)$$

$$\Theta_m = \frac{Q_m X_m}{\sum_n Q_n X_n} \quad (13)$$

$$\Psi_{mn} = \exp\left(-\frac{U_{mn} - U_{nn}}{RT}\right) = \exp\left(-\frac{a_{mn}}{T}\right) \quad (14)$$

where $\Theta_m$ is the area fraction of group m, and can be calculated in a way similar to $\theta_i$, $X_m$ is the mole fraction of group m in the mixture. $\Psi T_{mn}$ is the group interaction parameter, $U_{mn}$ is a measure of the interaction energy between groups m and n. $a_{mn}$ is the asymmetric group-interaction parameter obtained from fitting experimental phase equilibrium data.

Based on the aggregation thermodynamics, asphaltene solubility is calculated and compared with the experimental data reported by Mannistu et al.[16] for asphaltene solubility in 15 binary solvents. For comparison purpose, the inventors also present the asphaltene solubility calculation results based on the classic crystallization thermodynamics. The activity coefficients of molecular asphaltene and nanoaggregates are calculated with UNIFAC. The makeup of the UNIFAC functional groups for the solvents and the asphaltene molecule and the corresponding UNIFAC group parameters[34], i.e., $R_k$, $Q_k$, are given in Table 1.

TABLE 1

UNIFAC groups and group parameters for solvents and asphaltene molecules[34]

| Group | ACH | AC | ACCH | ACCH2 | ACCH3 | CH3 | CH2 | CH |
|---|---|---|---|---|---|---|---|---|
| $R_k$ | 0.5313 | 0.3652 | 0.8121 | 1.0396 | 1.2663 | 0.9011 | 0.6744 | 0.4469 |
| $Q_k$ | 0.400 | 0.120 | 0.348 | 0.660 | 0.968 | 0.848 | 0.540 | 0.228 |
| Asphaltene | 7 | 16 | 3 | 3 | | 9 | 13 | 3 |
| Toluene | 5 | | | | 1 | | | |
| n-Pentane | | | | | | 2 | 3 | |
| n-Hexane | | | | | | 2 | 4 | |
| n-Heptane | | | | | | 2 | 5 | |
| n-Octane | | | | | | 2 | 6 | |
| n-Decane | | | | | | 2 | 8 | |
| Isopentane | | | | | | 3 | 1 | 1 |
| Isooctane | | | | | | 5 | 1 | 1 |
| Acetone | | | | | | 1 | | |
| Methanol | | | | | | | | |
| 1-Hexene | | | | | | 1 | 3 | |
| Nitrobenzene | 5 | | | | | | | |
| t-Butylbenzene | 5 | 1 | | | | 3 | | |
| Cyclohexane | | | | | | | 6 | |
| Decalin | | | | | | | 8 | 2 |
| Dichloromethane | | | | | | | | |

| Group | C | CH2SH | CHNH | CH3CO | CH3OH | CH2=CH | ACNO2 | CH2Cl2 |
|---|---|---|---|---|---|---|---|---|
| $R_k$ | 0.2195 | 1.6510 | 0.9795 | 1.6724 | 1.4311 | 1.3454 | 1.4199 | 2.2564 |
| $Q_k$ | 0 | 1.368 | 0.624 | 1.448 | 1.432 | 1.176 | 1.104 | 1.998 |
| Asphaltene | | 1 | 1 | | | | | |
| Toluene | | | | | | | | |

TABLE 1-continued

UNIFAC groups and group parameters for solvents and asphaltene molecules[34]

| | | | | | | | |
|---|---|---|---|---|---|---|---|
| n-Pentane | | | | | | | |
| n-Hexane | | | | | | | |
| n-Heptane | | | | | | | |
| n-Octane | | | | | | | |
| n-Decane | | | | | | | |
| Isopentane | | | | | | | |
| Isooctane | 1 | | | | | | |
| Acetone | | | | 1 | | | |
| Methanol | | | | | 1 | | |
| 1-Hexene | | | | | | 1 | |
| Nitrobenzene | | | | | | | 1 |
| t-Butylbenzene | 1 | | | | | | |
| Cyclohexane | | | | | | | |
| Decalin | | | | | | | |
| Dichloromethane | | | | | | | 1 |

The UNIFAC group interaction parameters[30,34] are given in Table 2.

TABLE 2

UNIFAC Group-interaction parameters[30,34]

| Group i/j | ACH | AC | ACCH | ACCH2 | ACCH3 | CH3 | CH2 | CH |
|---|---|---|---|---|---|---|---|---|
| ACH | 0 | 0 | 167 | 167 | 167 | −11.12 | −11.12 | −11.12 |
| AC | 0 | 0 | 167 | 167 | 167 | −11.12 | −11.12 | −11.12 |
| ACCH | −146.8 | −146.8 | 0 | 0 | 0 | −69.7 | −69.7 | −69.7 |
| ACCH2 | −146.8 | −146.8 | 0 | 0 | 0 | −69.7 | −69.7 | −69.7 |
| ACCH3 | −146.8 | −146.8 | 0 | 0 | 0 | −69.7 | −69.7 | −69.7 |
| CH3 | 61.13 | 61.13 | 76.5 | 76.5 | 76.5 | 0 | 0 | 0 |
| CH2 | 61.13 | 61.13 | 76.5 | 76.5 | 76.5 | 0 | 0 | 0 |
| CH | 61.13 | 61.13 | 76.5 | 76.5 | 76.5 | 0 | 0 | 0 |
| C | 61.13 | 61.13 | 76.5 | 76.5 | 76.5 | 0 | 0 | 0 |
| CH2SH | 28.41 | 28.41 | 19.56 | 19.56 | 19.56 | −7.481 | −7.481 | −7.481 |
| CHNH | −22.31 | −22.31 | 223 | 223 | 223 | 65.33 | 65.33 | 65.33 |
| CH3CO | 140.1 | 140.1 | 365.8 | 365.8 | 365.8 | 26.76 | 26.76 | 26.76 |
| CH3OH | −50 | −50 | −44.5 | −44.5 | −44.5 | 16.51 | 16.51 | 16.51 |
| CH2═CH | 38.81 | 38.81 | 74.15 | 74.15 | 74.15 | −35.36 | −35.36 | −35.36 |
| ACNO2 | 1824 | 1824 | −127.8 | −127.8 | −127.8 | 5541 | 5541 | 5541 |
| CH2Cl2 | 121.3 | 121.3 | 140.8 | 140.8 | 140.8 | 34.01 | 34.01 | 34.01 |

| Group i/j | C | CH2SH | CHNH | CH3CO | CH3OH | CH2═CH | ACNO2 | CH2Cl2 |
|---|---|---|---|---|---|---|---|---|
| ACH | −11.12 | −10.43 | 122.8 | 25.77 | 637.4 | 3.446 | 194.9 | −144.4 |
| AC | −11.12 | −10.43 | 122.8 | 25.77 | 637.4 | 3.446 | 194.9 | −144.4 |
| ACCH | −69.7 | 393.6 | −49.29 | −52.1 | 603.2 | −113.6 | 4448 | −111 |
| ACCH2 | −69.7 | 393.6 | −49.29 | −52.1 | 603.2 | −113.6 | 4448 | −111 |
| ACCH3 | −69.7 | 393.6 | −49.29 | −52.1 | 603.2 | −113.6 | 4448 | −111 |
| CH3 | 0 | 184.4 | 255.7 | 476.4 | 697.2 | 86.02 | 543 | 53.76 |
| CH2 | 0 | 184.4 | 255.7 | 476.4 | 697.2 | 86.02 | 543 | 53.76 |
| CH | 0 | 184.4 | 255.7 | 476.4 | 697.2 | 86.02 | 543 | 53.76 |
| C | 0 | 184.4 | 255.7 | 476.4 | 697.2 | 86.02 | 543 | 53.76 |
| CH2SH | −7.481 | 0 | 0 | 160.6 | 448.6 | 0 | 0 | 0 |
| CHNH | 65.33 | 0 | 0 | 394.6 | −370.3 | −28.7 | 0 | 0 |
| CH3CO | 26.76 | −46.28 | −174.2 | 0 | 108.7 | 42.92 | 548.5 | −130.3 |
| CH3OH | 16.51 | 17.5 | −20.98 | 23.39 | 0 | −12.52 | 457.9 | −102.5 |
| CH2═CH | −35.36 | 0 | 163.9 | 182.6 | 787.6 | 0 | 0 | 58.55 |
| ACNO2 | 5541 | 0 | 0 | −101.5 | 511.3 | 0 | 0 | 0 |
| CH2Cl2 | 34.01 | 0 | 0 | 82.86 | 669.9 | −23.5 | 0 | 0 |

Crystallization formulation. If the asphaltene precipitation were a crystallization process, Eq. (1) should be followed and the logarithm of solubility product constant $K_{sp}$ would be calculated as $$\ln K_{sp} = \ln x_{asp}^{sat} + \ln \gamma_{asp}^{sat} \quad (15)$$

where superscript sat stands for asphaltene saturation per the crystallization process.

As derived from Gibbs-Helmholtz equation, the solubility product constant at a specified temperature is determined by heat of fusion $\Delta H_{fus}^0(T_m)$ and melting temperature $T_m$, expressed as follows[35].

$$\ln K_{sp} = \frac{\Delta G_{cryst}^0(T)}{RT} = -\frac{\Delta G_{fus}^0(T)}{RT} = \frac{\Delta H_{fus}^0(T_m)}{R}\left[\frac{1}{T_m} - \frac{1}{T}\right] \quad (16)$$

For "pure" asphaltenes forming the same "crystalline" polymorph, $\Delta H_{fus}^0(T_m)$ and $T_m$ are constant, i.e., $K_{sp}$ should be the same for asphaltene "crystallization" in all solvents and solvent combinations at a specified temperature. The inventors used the data of Mannistu et al.[16], who determined the solubility of purified asphaltene from Athabasca bitumen by using both solubility and precipitation methods. Next, 15 sets of asphaltene solubility data in binary solvents were reported. These binary solvents were assigned as toluene with poor solvents (n-pentane, n-hexane, n-heptane, n-octane, n-decane, isopentane, isooctane, 1-hexene, acetone, methanol) and n-hexane with good solvents (nitrobenzene, tert-butylbenzene, decalin, cyclohexane, dichloromethane). For all cases, asphaltene initial concentration was 8.8 kg/m$^3$ and the mass ratio of insoluble asphaltene fraction to total asphaltene was measured with the binary solvent compositions varied. In the solubility method, asphaltenes were added to a premixed known ratio of a good solvent and a poor solvent. In the precipitation method, asphaltenes were first dissolved in the good solvent before the poor solvent was added. Note that a common feature for all the 15 sets of experimental data is that asphaltene becomes more soluble as the good solvent (toluene, dichloromethane, nitrobenzene, tert-butylbenzene, cyclohexane, and decalin) concentration increases. Table 3 summarizes the data of Mannistu et al.[16] and the calculated results of ln $K_{sp}$ from Eq. (15) for the 15 binary solvents. The calculated ln $K_{sp}$ for asphaltene "crystallization" varies over a wide range from −13 to −6.

With a range of −11.20∼−10.52, the calculated ln $K_{sp}$ for asphaltene "crystallization" in the toluene+n-hexane binary solvent is relatively constant. To further examine the solubility predictions based on the "crystallization" thermodynamics, the inventors assumed the average ln $K_{sp}$ of asphaltene solubility in the toluene+n-hexane binary, i.e. −10.74, and predict with UNIFAC the asphaltene solubility in all 15 binary solvents. The errors in ln x of solubility are calculated for the 15 binary solvents by the following expression:

$$\Delta \ln x = |\ln x_{exp} - \ln x_{est}| \quad (17)$$

where subscript exp and est represent experimental and model predicted asphaltene saturation concentration, respectively. Results are summarized in Table 3. Due to possibly higher uncertainties for the data points with mass ratio of insoluble subfraction of asphaltenes near zero, those data points with the insoluble subfraction less or around 0.1 are excluded from the Δ ln x calculations. The comparison between the experimental solubility data[16] and the model predicted results are shown in FIGS. 3 to 5.

Figure 3:
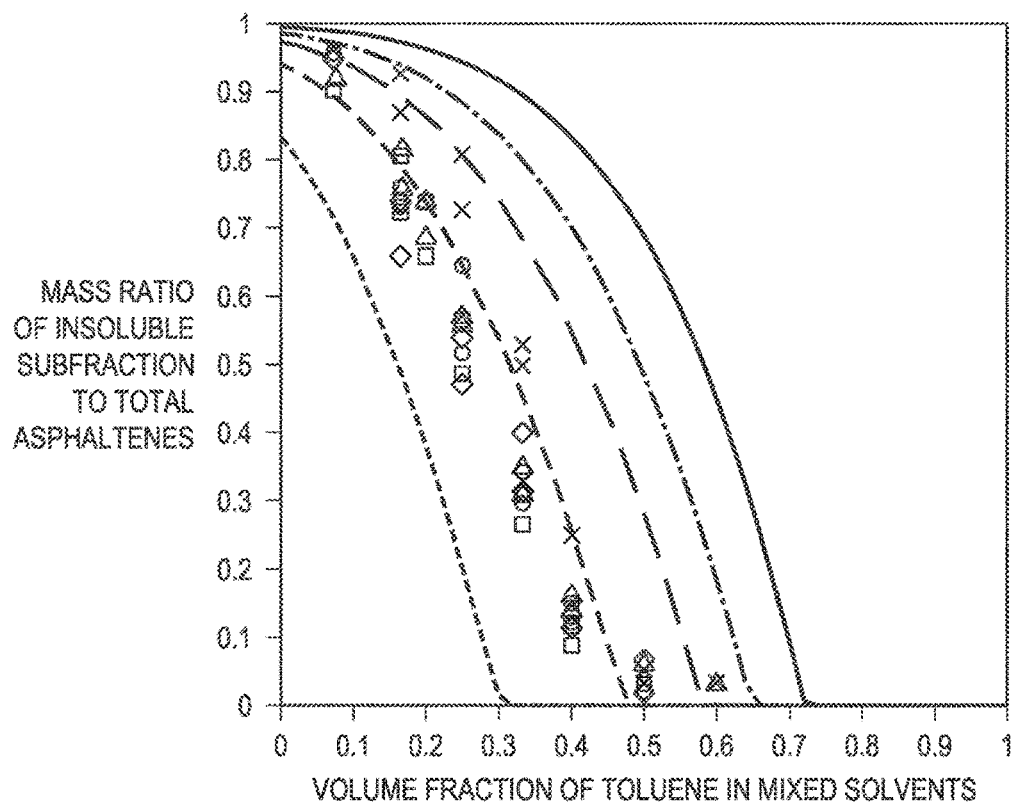
FIG. 3 is a comparison of asphaltene solubility between experimental data (symbols)[16] and "crystallization" model predicted results (lines) in binary solvents of toluene+ isopentane (line of small dashes), isooctane (line of large dashes), acetone (solid line), methanol (line of alternating dashes and dots), and 1-hexene (line of medium size dashes)

FIG. 3 shows the results for the binary solvents of toluene with n-pentane, n-hexane, n-heptane, n-octane, and n-decane. The model predictions capture well the trend of increasing asphaltene solubility with increasing toluene content. But more importantly, the experimental data of asphaltene solubility show a trend of slightly increasing asphaltene solubility with increasing carbon number of n-alkane solvents[16]. This trend has also been reported by Wiehe et al.[36]. In measuring asphaltene precipitation by adding n-paraffin to various crude samples, they concluded that the asphaltene solubility increases as the n-alkane carbon number increases up to a maximum at 9 or 10, and then decreases. Contrary to the trend exhibited by the data, the "crystallization" thermodynamics suggests the asphaltene solubility should decrease with increasing n-paraffin carbon number.

Figure 4:
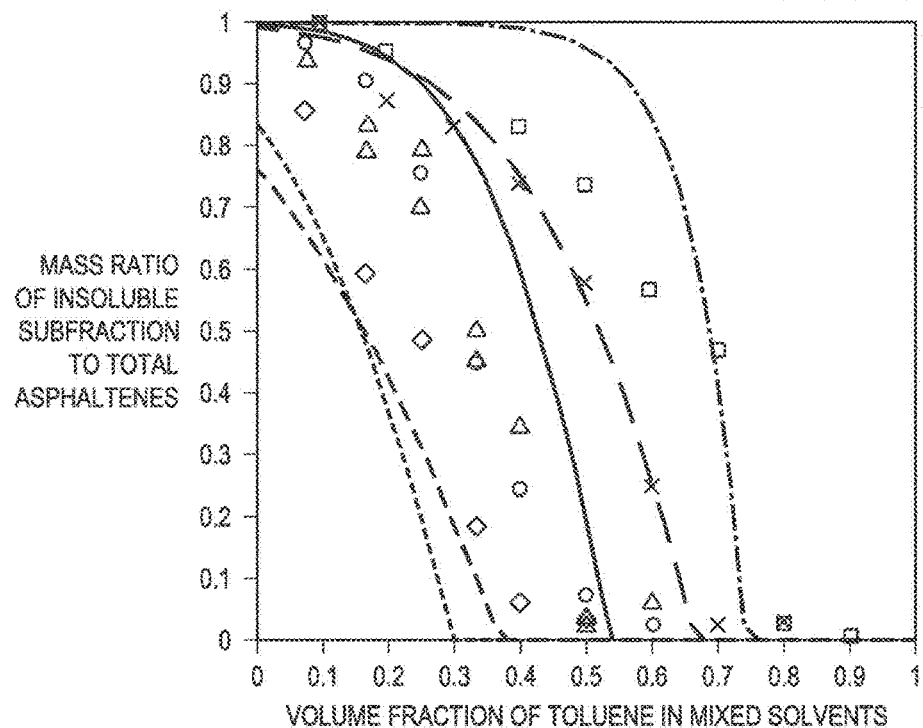
FIG. 4 is a comparison of asphaltene solubility between experimental data (symbols)[16] and "crystallization" model predicted results (lines) in binary solvents of n-hexane+good solvent: dichloromethane (line of small dashes), nitrobenzene (line of medium size dashes), tert-butylbenzene (line of large dashes), decalin (line of alternating dashes and dots), and cyclohexane (solid line)

FIG. 4 shows the predicted asphaltene solubility in another five sets of binary solvents of toluene with two branched alkanes (isopentane and isooctane), two polar solvents (acetone and methanol), and an olefin (1-hexene). Still the "crystallization" thermodynamics captures the trend of increasing asphaltene solubility with increasing toluene content. However, it fails to predict the trend of increasing asphaltene solubility with increasing carbon number for the two iso-paraffins, i.e., isopentene and isooctane.

Figure 5:
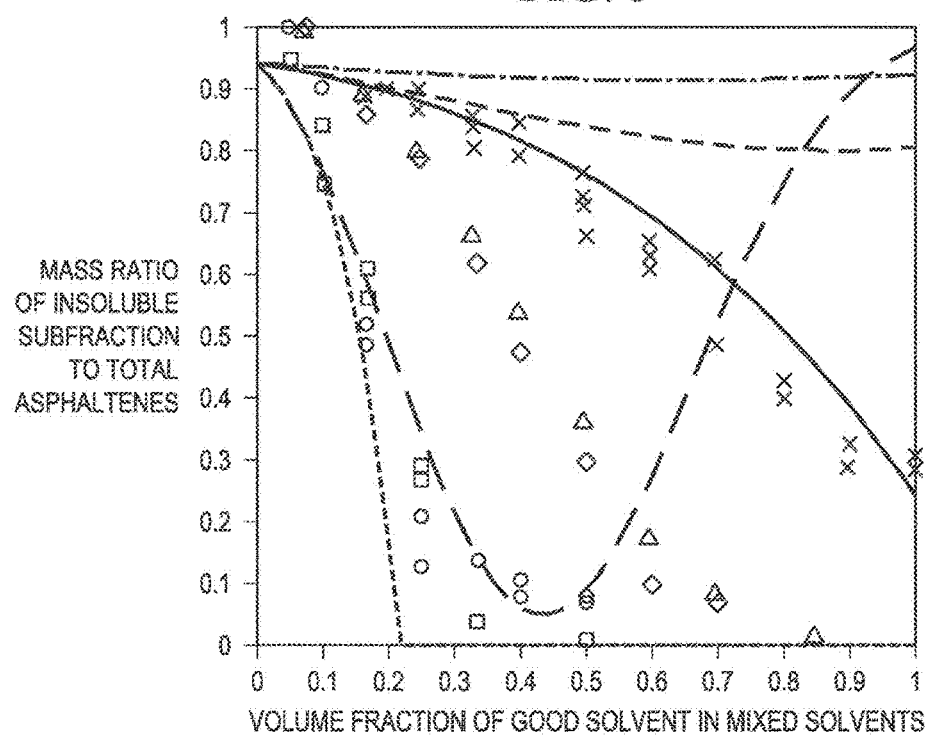
FIG. 5 is a graph showing a comparison of asphaltene solubility between experimental data (symbols)[16] and "crystallization" model predicted results (lines) in binary solvents of n-hexane+good solvent: dichloromethane (line of small dashes and open squares, respectively), nitrobenzene (line of large dashes and open circles, respectively), tert-butylbenzene (line of medium dashes and open triangles, respectively), decalin (line of dots and large dashes and open diamonds, respectively), and cyclohexane (solid line and exes, respectively).

FIG. 5 shows the predicted asphaltene solubility in the third five sets of binary solvents of n-hexane with good solvents, including dichloromethane, nitrobenzene, tert-butylbenzene, cyclohexane and decalin. The predictions for asphaltene solubility in the binary solvents of n-hexane with dichloromethane and with cyclohexane are in good agreement with the data. However, UNIFAC incorrectly predicts nitrobenzene, tert-butylbenzene, and decalin as poor solvents. Interestingly, UNIFAC predicts enhanced asphaltene solubilities in the n-hexane+nitrobenzene binary when the n-hexane volume fraction reaches around 0.4 to 0.5.

Aggregation formulation. To apply the aggregation thermodynamics, follow Eq. (4) and calculate the equivalent solubility product constant $K_{sp}^{agg}$ as follows.

$$\ln K_{sp}^{agg} = \ln K_{sp} + \ln \gamma_{nano}^{\infty} = \ln x_{asp}^{agg} + \ln \gamma_{asp}^{agg} \quad (18)$$

or $$\ln x_{asp}^{agg} = \ln K_{sp} - (\ln \gamma_{asp}^{agg} - \ln \gamma_{nano}^{\infty}) \quad (19)$$

Clearly the difference between the "crystallization" thermodynamics and the aggregation thermodynamics is ln $\gamma_{nano}^{\infty}$, the logarithm of activity coefficient of asphaltene nanoaggregates in infinite dilution. According to UNIFAC, ln $\gamma_{nano}^{\infty}$ is determined by both the entropic and the enthalpic effects. The entropic effect is from mixing the alkyl side chains of asphaltene nanoaggregates with the solvents, and the enthalpic effect is due to the physical interaction between the alkyl side chains and the solvents.

Figure 6:
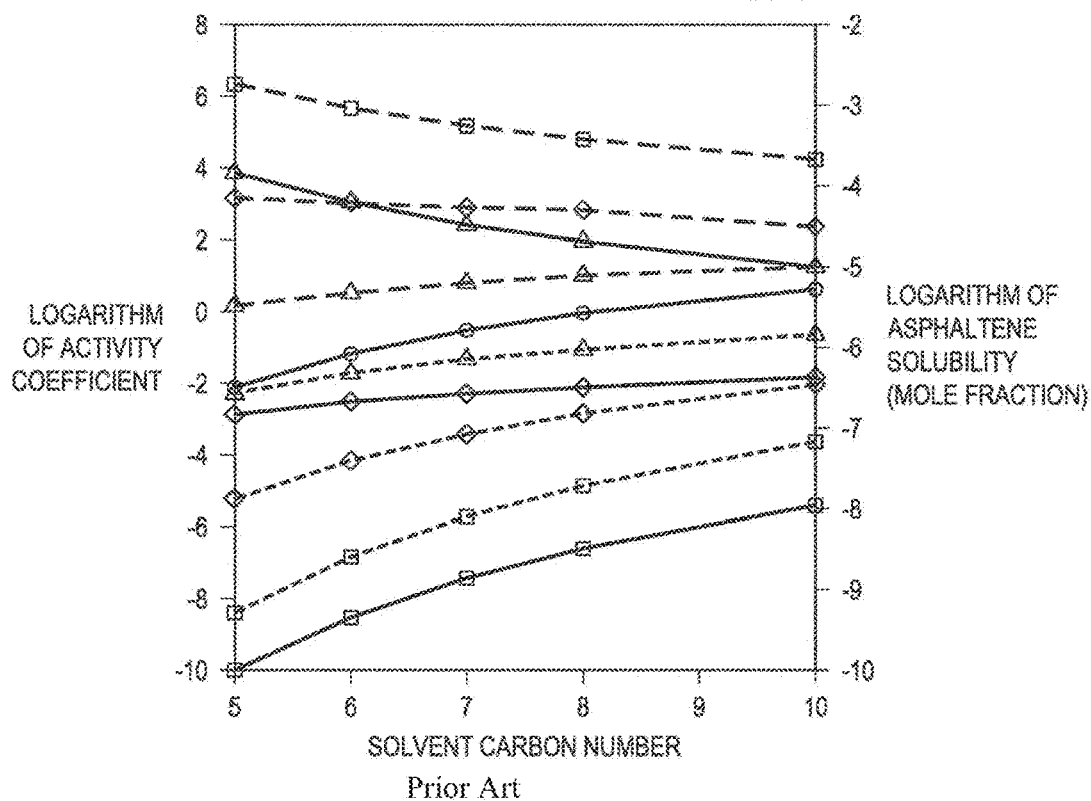
FIG. 6 shows the effect of representative nanoaggregate effective alkyl side chain length on activity coefficients and asphaltene solubility. Representative nanoaggregate alkyl side chains as n-$C_{28}H_{58}$ (solid line with triangles, medium dashed line with triangles, and small dashed line with triangles), n-$C_{49}H_{100}$ (solid line with diamonds, medium dashed line with diamonds, small dashed line with diamonds), and n-$C_{70}H_{142}$ (solid line with open squares, medium dashed line with open squares, small dashed line with open squares). In $\gamma_{asp}^{agg}$ (solid line with open circle), ln $\gamma_{nano}^{\infty}$ (small dotted lines with open triangle, open diamond and open square), (ln $\gamma_{asp}^{agg}$–ln $\gamma_{nano}^{\infty}$) (medium dashed lines with open square, open diamond and open triangle), ln $x_{asp}^{agg}$ (solid lines with open triangle, open diamond and open square) while assuming ln $K_{sp}$=–3.70.

To examine the effect of ln $\gamma_{nano}^{\infty}$, the inventors took a closer look at the trend observed by Wiehe et al.[36] and shown as data in FIG. 3 that asphaltene solubility should increase slightly as n-alkane solvent carbon number increases from five to ten. The observation suggests that, since ln $K_{sp}$ should be constant, (ln $\gamma_{asp}^{agg}$ − ln $\gamma_{nano}^{\infty}$) should decrease with increase in the n-alkane solvent carbon number. Moreover, since these n-alkane solvents and the nanoaggregate alkyl side chains are of same chemical nature, the entropic effect should dominate. The inventors varied the "effective" chain length of the representative asphaltene nanoaggregate alkyl side chains and examine how (ln $\gamma_{asp}^{agg}$ − ln $\gamma_{nano}^{\infty}$) would change with increase in the n-alkane solvent carbon number. FIG. 6 shows the calculated values for ln $\gamma_{asp}^{agg}$, ln $\gamma_{nano}^{\infty}$, and (ln $\gamma_{asp}^{agg}$ − ln $\gamma_{nano}^{\infty}$) for the alkyl side chains assuming "effective" chain length or carbon number of 28, 49, and 70. It is found that (ln $\gamma_{asp}^{agg}$ − ln $\gamma_{nano}^{\infty}$) increases with increase in the solvent carbon number if the effective carbon number for the nanoaggregate side chains is small, i.e., 28. The (ln $\gamma_{asp}^{agg}$ − ln $\gamma_{nano}^{\infty}$) term becomes relatively constant with change in the solvent carbon number when the nanoaggregate effective carbon number reaches 49. When the effective carbon number goes up to 70, the trend of (ln $\gamma_{asp}^{agg}$ − ln $\gamma_{nano}^{\infty}$) vs. the solvent carbon number reverses. The effective carbon of ∼70 seems reasonable when the number of asphaltene molecules in the nanoaggregate is ∼6[11] is considered, assuming the average carbon number for the alkyl side chain is ∼12 per asphaltene molecule. With the effective carbon number fixed at 70, the calculated solubility complies with the solubility trend observed by Wiehe et al.[36] with increasing the n-alkane solvent carbon number and matches the data of Mannistu et al.[16] when using ln $K_{sp}$=−3.70.

Figure 7:
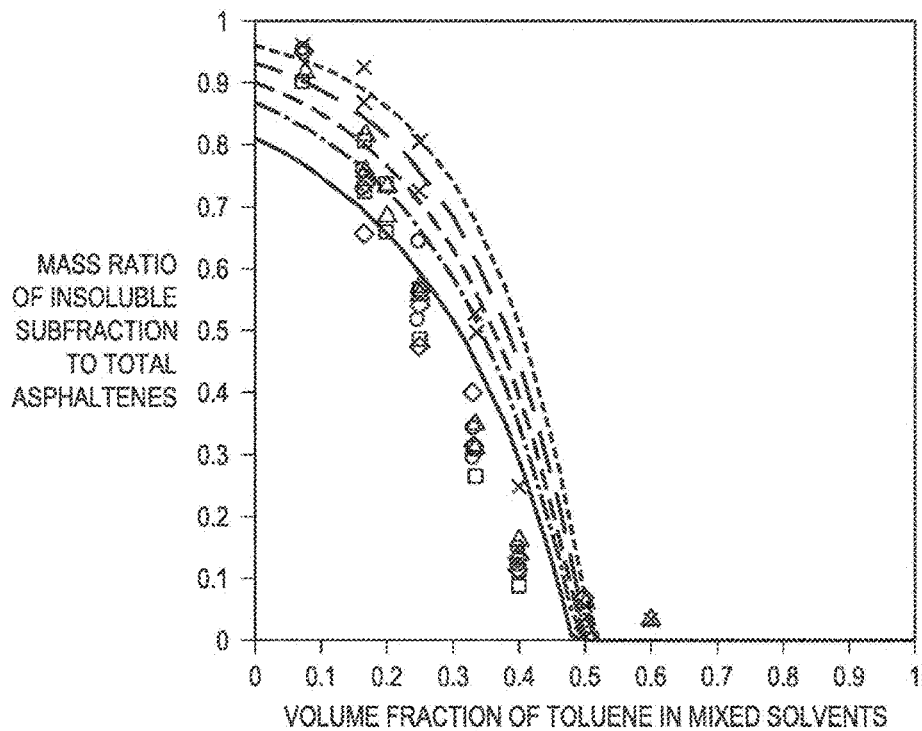
FIG. 7 is a comparison of asphaltene solubility between experimental data (symbols)[16] and aggregation model predicted results (lines) in binary solvents of toluene+n-pentane (exes and line of small dashes), n-hexane (triangles and line of large size dashes), n-heptane (open squares and line of medium dashes), n-octane (open circles and line of alternating dashes and dots), and n-decane (open diamonds and solid line)

With the effective carbon number and ln $K_{sp}$ fixed at 70 and −3.70 respectively, the average errors in ln x of the solubility calculated for the 15 solvents are summarized in Table 3. In comparison to the results of "crystallization" thermodynamics, significant improvement in the predicted asphaltene solubility notably for the alkane solvents is obtained with the aggregation thermodynamics. The inventors also show comparisons between the experimental solubility data and the model prediction results for all 15 binary solvents in FIGS. 7 to 9. In FIG. 7, the aggregation thermodynamics together with UNIFAC successfully predicts the asphaltene solubility in the binary solvents of toluene and n-alkanes. The predictions capture well the trend of increasing asphaltene solubility with increasing toluene content. Moreover, the predicted asphaltene solubility increases as the n-alkane solvent carbon number varies from five to ten.

with toluene. It appears that, for the methanol+toluene binary solvent, UNIFAC correctly predicts high positive ln $\gamma_{nano}^\infty$ but probably much overestimates ln $\gamma_{nano}^\infty$ for the high methanol volume fraction region (toluene volume fraction<0.3). Specifically, UNIFAC predict ln $\gamma_{nano}^\infty$ to be >12 in pure methanol, ~−5 in toluene, and ~−7 in n-hexane. It seems UNIFAC overestimates ln $\gamma_{nano}^\infty$ for high methanol fraction region and therefore overestimates asphaltene solubility. Although not shown here, similar phenomenon is observed for the acetone+toluene binary solvent.

The overestimation of UNIFAC for ln $\gamma_{nano}^\infty$ for high methanol fraction region and high acetone region could be attributed to the formation of methanol dimers and acetone dimers. Gómez-Álvarez et al.[37] conducted Monte Carlo

TABLE 3

Logarithm of solubility product constant of asphaltene molecules in 15 binary solvents.

| Good solvent | Poor solvent | Volume ratio of good solvent to mixed solvent | Number of data points | ln $K_{sp}$ range assuming crystallization process | Average Δ ln x with ln $K_{sp}$ = −10.74 assuming crystallization process | Average Δ ln x with ln $K_{sp}$ = −3.70 assuming aggregation process |
|---|---|---|---|---|---|---|
| Toluene | n-Pentane | 0.073~0.60 | 11 | −12.66~−11.40 | 1.055 | 0.263 |
| Toluene | n-Hexane | 0.072~0.48 | 14 | −11.20~−10.52 | 0.160 | 0.244 |
| Toluene | n-Heptane | 0.072~0.39 | 12 | −10.43~−9.737 | 0.791 | 0.166 |
| Toluene | n-Octane | 0.070~0.48 | 11 | −10.30~−9.272 | 1.159 | 0.312 |
| Toluene | n-Decane | 0.071~0.48 | 11 | −9.625~−8.272 | 1.918 | 0.522 |
| Toluene | Isopentane | 0.073~0.601 | 7 | −12.88~−11.40 | 1.187 | 0.352 |
| Toluene | Isooctane | 0.075~0.500 | 11 | −10.51~−9.255 | 1.034 | 0.474 |
| Toluene | Acetone | 0.197~0.800 | 7 | −11.78~−9.897 | 0.439 | —[a] |
| Toluene | Methanol | 0.196~0.902 | 7 | −12.44~−6.698 | 1.973 | —[a] |
| Toluene | 1-Hexene | 0.071~0.501 | 6 | −9.168~−8.176 | 2.021 | 1.687 |
| Nitrobenzene | n-Hexane | 0.099~0.502 | 10 | −11.58~−10.45 | 0.338 | 0.993 |
| tert-Butylbenzene | n-Hexane | 0.160~0.846 | 9 | −13.22~−9.131 | 1.355 | 0.506 |
| Cyclohexane | n-Hexane | 0.165~1.000 | 24 | −10.92~−10.40 | 0.143 | 0.811 |
| Decalin | n-Hexane | 0.167~0.701 | 7 | −10.03~−8.340 | 1.457 | 0.613 |
| Dichloromethane | n-Hexane | 0.051~0.500 | 9 | −13.05~−10.74 | 0.376 | 0.619 |

[a] Model failed to predict solubility.

Figure 8:
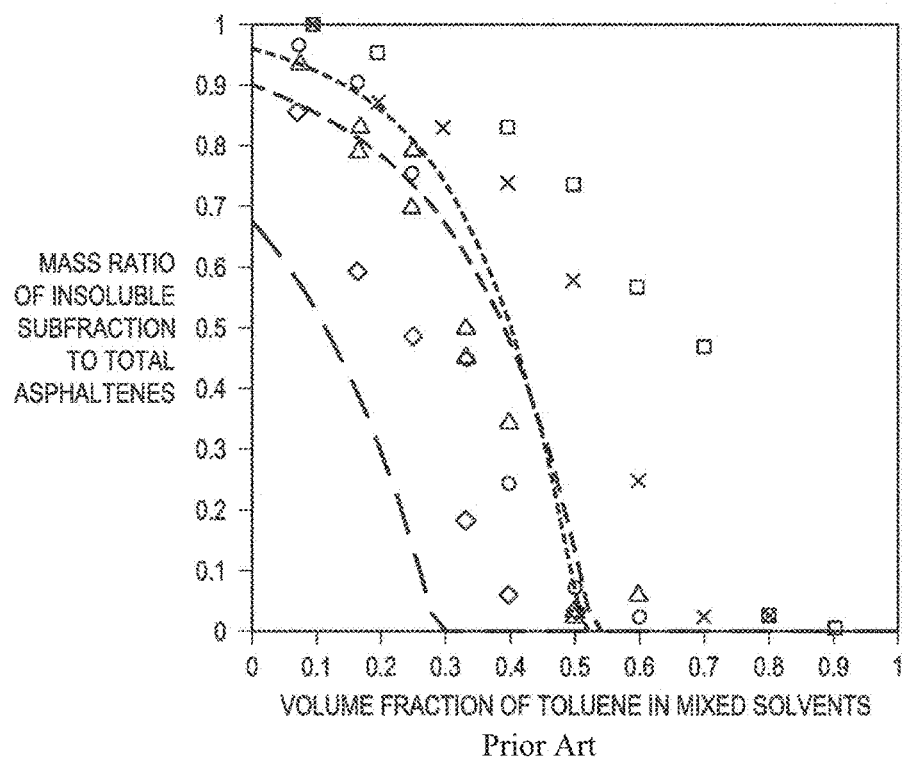
FIG. 8 is a comparison of asphaltene solubility between experimental data (symbols)[16] and aggregation model predicted results (lines) in binary solvents of toluene+isopentane (open circles and line of small dashes), isooctane (open triangles and line of medium dashes), acetone (exes), methanol (open squares), and 1-hexene (open diamonds and line of large dashes)

FIG. 8 shows excellent model predictions for asphaltene solubility in the binary solvents of toluene with branched alkanes (isopentane and isooctane). The model correctly predicts the trend of increasing asphaltene solubility with increasing carbon number for the two iso-paraffins. The model also yields qualitatively correct predictions for asphaltene solubility in the binary solvent of toluene with 1-hexene. However, the model fails to predict asphaltene solubility in toluene with acetone and with methanol. It incorrectly predicts acetone and methanol as good solvents for asphaltene.

Figure 9:
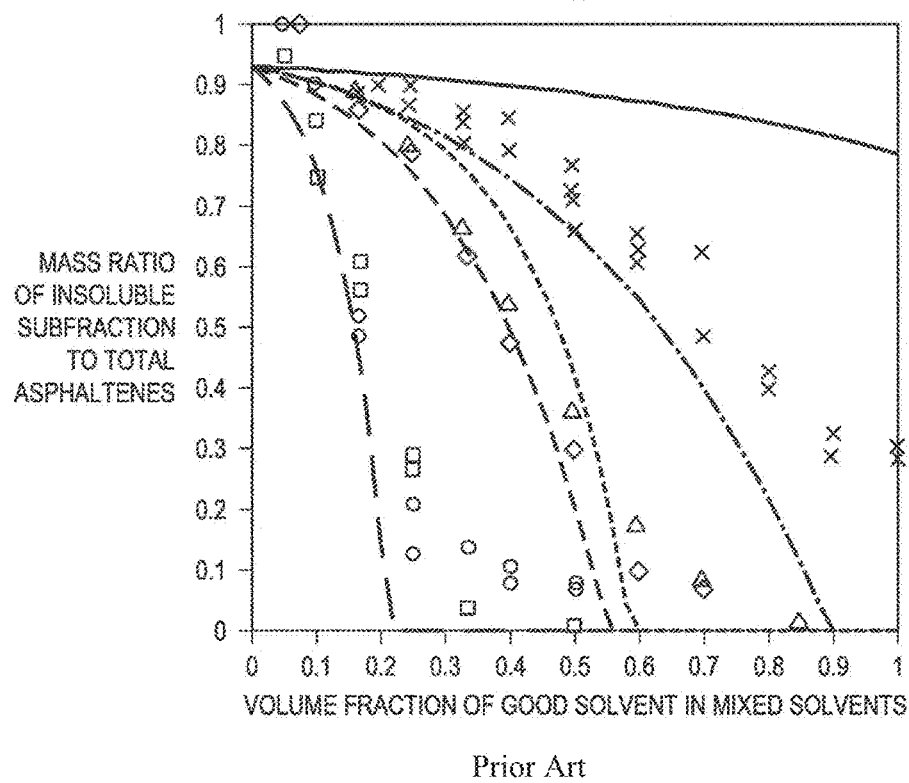
FIG. 9 is a comparison of asphaltene solubility between experimental data (symbols)[16] and aggregation model predicted results (lines) in binary solvents of n-hexane+good solvent: dichloromethane (open squares and line of small dashes), nitrobenzene (open circles and line of large size dashes), tert-butylbenzene (triangles and line of medium dashes), decalin (open diamonds and line of alternating dashes and dots), and cyclohexane (exe and solid line)

FIG. 9 shows the aggregation thermodynamics gives qualitatively correct predictions of asphaltene solubility in the binary solvents of n-hexane with five good solvents including dichloromethane, nitrobenzene, tert-butylbenzene, cyclohexane and decalin. Unlike the "crystallization" model, which incorrectly predicts nitrobenzene, tert-butylbenzene, and decalin as poor solvents, the aggregation model properly predicts these five solvents as good solvents. While the average errors in ln x of solubility calculated for the five binary solvents are significant, given the predictive nature of UNIFAC, the qualitative agreement between the data and the model results is considered satisfactory.

Figure 10:
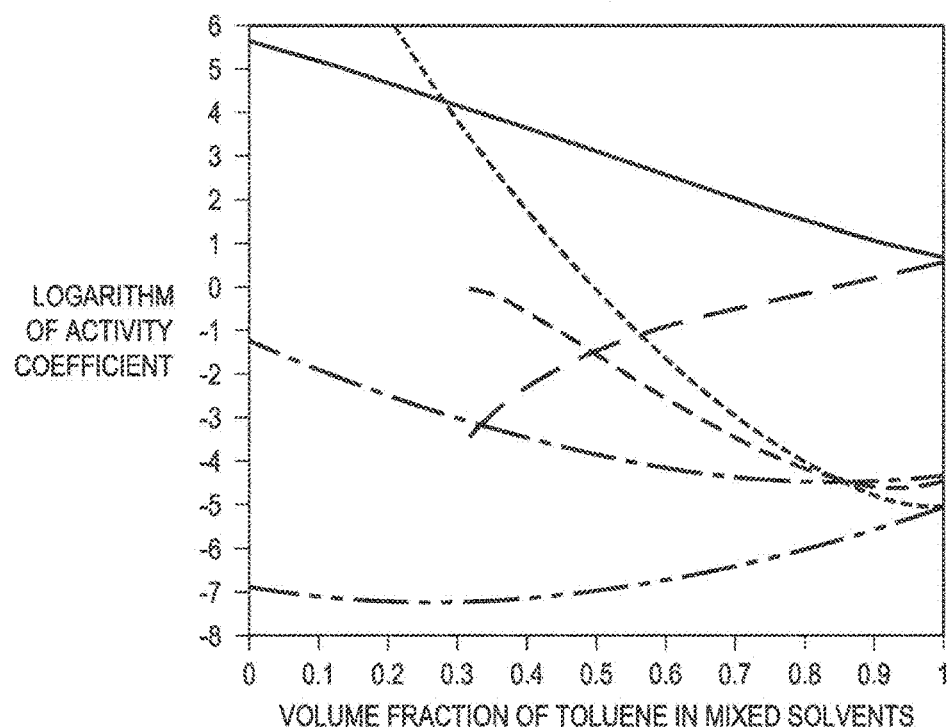
FIG. 10 shows a model predicted activity coefficients for molecular asphaltene and nanoaggregates in infinite dilution. n-hexane+toluene binary solvent (solid line, short and long dashes, and double short and long hash lines), methanol+toluene binary solvent (lines of small, medium and large size dashes). ln $\gamma_{asp}^{agg}$ (medium dashed line and short and long dashes), ln $\gamma_{nano}^{\infty}$ (small dashed line and double short and long hash lines), (ln $\gamma_{asp}^{agg}$–ln $\gamma_{nano}^{\infty}$) (solid line and large hashed line)

To examine further the model predictions for asphaltene solubility in toluene with methanol, FIG. 10 shows a comparison of model predicted activity coefficients for two binary solvent systems, n-hexane with toluene and methanol simulation and showed that a linearly hydrogen bonded dimer is the most probable associated state for pure methanol. Hermida-Ramón and Rios[38] also found the most stable state for acetone molecules is the dimer formed by two antiparallel monomers being linked by four hydrogen bonds. This formation of dimers should greatly reduce the amount of exposed —OH group for methanol and =O group for acetone. This reduction in these hydrogen bond-forming groups probably could be better accounted for by UNIFAC in the calculation of ln $\gamma_{nano}^\infty$.

To better illustrate the three proposed forms of asphaltene, the Gibbs free energy of asphaltene molecules is calculate in solution, "nanocrystals", and nanoaggregates in the solvents. The results are shown in Table 4 and plotted in FIG. 11. Here the reference state is chosen to be "liquid" asphaltene molecules, and the Gibbs free energies of other asphaltene forms are obtained from following expressions.

$$\text{For asphaltene molecules in solution: } \frac{\Delta G}{RT} = \ln \gamma_{asp}^{agg} \quad (20)$$

$$\text{For "nanocrystals": } \frac{\Delta G}{RT} = \ln K_{sp} \quad (21)$$

$$\text{For nanoaggregates } \frac{\Delta G}{RT} = \ln K_{sp} + \ln \gamma_{nano}^\infty \quad (22)$$

TABLE 4

Calculated results of logarithm of activity coefficient ln γ and Gibbs free energy $\frac{\Delta G}{RT}$ of asphaltene existing in different forms

| Pure solvent | $\frac{\Delta G}{RT}$ for molecular "liquid" asphaltene | $\ln\gamma_{asp}^{agg}$ at $x_{asp}^{agg}$ | $\frac{\Delta G}{RT}$ for asphaltene molecule in solution | $\frac{\Delta G}{RT}$ for "nanocrystal" | $\ln\gamma_{nano}^{\infty}$ | $\frac{\Delta G}{RT}$ for nanoaggregate |
|---|---|---|---|---|---|---|
| Toluene | 0 | −4.434 | −4.434 | −3.70 | −5.019 | −8.719 |
| n-Pentane | 0 | −2.121 | −2.121 | −3.70 | −8.416 | −12.12 |
| n-Hexane | 0 | −1.216 | −1.216 | −3.70 | −6.864 | −10.56 |
| n-Heptane | 0 | −0.556 | −0.556 | −3.70 | −5.720 | −9.420 |
| n-Octane | 0 | −0.057 | −0.057 | −3.70 | −4.845 | −8.545 |
| n-Decane | 0 | 0.637 | 0.637 | −3.70 | −3.603 | −7.303 |
| Isopentane | 0 | −2.153 | −2.153 | −3.70 | −8.433 | −12.13 |
| Isooctane | 0 | 0.351 | 0.351 | −3.70 | −4.691 | −8.391 |
| Acetone | 0 | N.A.* | N.A.* | −3.70 | 5.665 | 1.965 |
| Methanol | 0 | N.A.* | N.A.* | −3.70 | 12.87 | 9.173 |
| 1-Hexene | 0 | −2.578 | −2.578 | −3.70 | −6.736 | −10.44 |
| Nitrobenzene | 0 | N.A.* | N.A.* | −3.70 | 11.48 | 7.783 |
| tert-Butylbenzene | 0 | −2.461 | −2.461 | −3.70 | −3.532 | −7.232 |
| Cyclohexane | 0 | −3.602 | −3.602 | −3.70 | −8.308 | −12.01 |
| Decalin | 0 | −1.654 | −1.654 | −3.70 | −4.219 | −7.919 |
| Dichloromethane | 0 | −5.445 | −5.445 | −3.70 | −5.568 | −9.268 |

*Calculated results are not available because asphaltenes are predicted to be completely dissolved in these solvents.
Therefore there are no predicted $x_{asp}^{agg}$ available to calculate the corresponding $\ln\gamma_{asp}^{agg}$ and $\frac{\Delta G}{RT}$ for asphaltene molecule in solution.

Figure 11:
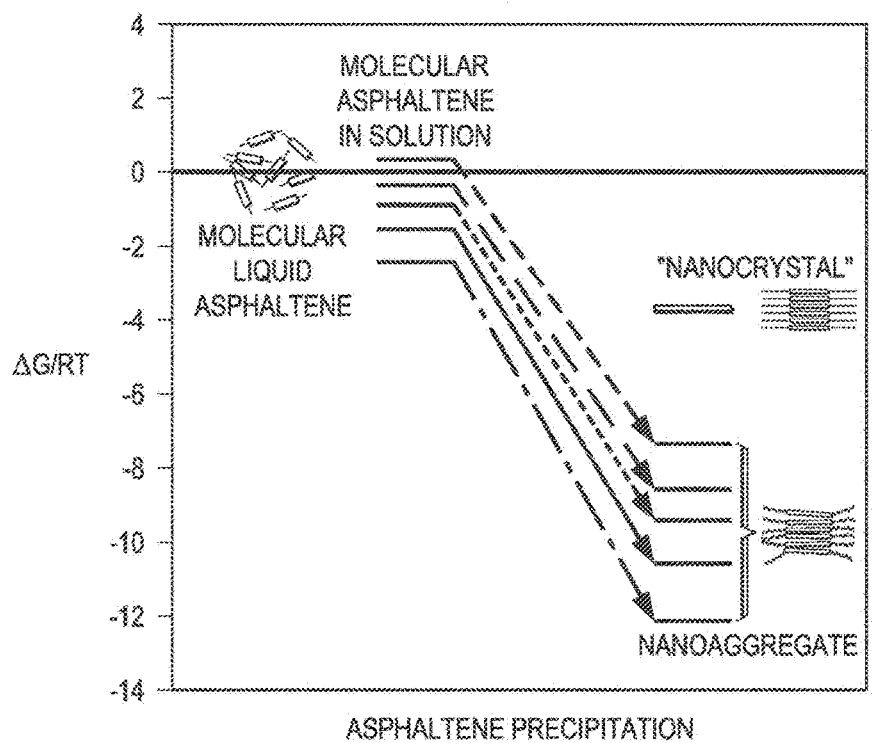
FIG. 11 shows the modeled results of Gibbs free energy of asphaltene in different forms calculated with aggregation formulation and UNIFAC. Pure solvents: n-pentane (line of alternating dashes and dots), n-hexane (solid line), n-heptane (line of small dashes), n-octane (line of medium size dashes), and n-decane (line of large dashes).

FIG. 11 shows that Gibbs free energy states of asphaltene molecules and nanoaggregates are functions of the solvents and the solvent compositions. Asphaltene nanoaggregates have much lower Gibbs free energy states compared to asphaltene molecules in n-alkanes, indicating nanoaggregates are a more favorable form than asphaltene molecules in n-alkanes.

Thus, the present invention includes a novel thermodynamic formulation is proposed for the onset of asphaltene precipitation consistent with the Yen-Mullins model. The aggregation thermodynamics coupled with UNIFAC for predicting the activity coefficients satisfactorily explain asphaltene solubility behavior in 13 of the 15 binary solvent systems covering wide varieties of chemical structures and full ranges of composition. Future studies should involve applications of more advanced activity coefficient models, further validation of the thermodynamic formulation with asphaltene solubility data in petroleum crudes, and extension to coal-derived asphaltenes.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Oh K, Ring T A, Deo M D. Asphaltene aggregation in organic solvents. Journal of Colloid and Interface Science. 2004; 271:212-219.
2. Akbarzadeh K, Alboudwarej H, Svrcek W Y, Yarranton H W. A generalized regular solution model for asphaltene precipitation from n-alkane diluted heavy oils and bitumens. Fluid Phase Equilibria. 2005; 232:159-170.
3. Aske N, Kallevik H, Sjöblom J. Determination of saturate, aromatic, resin, and asphaltenic (SARA) components in crude oils by means of infrared and near-infrared spectroscopy. Energy & Fuels. 2001; 15:1304-1312.
4. Yoon S, Bhatt S, Lee W, Lee H, Jeong S, Baeg J-O, Lee C. Separation and characterization of bitumen from Athabasca oil sand. Korean J. Chem. Eng. 2009; 26:64-71.
5. Zanganeh P, Ayatollahi S, Alamdari A, Zolghadr A, Dashti H, Kord S. Asphaltene deposition during CO2 injection and pressure depletion: a visual study. Energy & Fuels. 2012; 26:1412-1419.
6. Tharanivasan A K, Svrcek W Y, Yarranton H W, Taylor S D, Merino-Garcia D, Rahimi P M, Measurement and modeling of asphaltene precipitation from crude oil blends. Energy & Fuels. 2009; 23:3971-3980.
7. Rassamdana H, Dabir B, Nematy M, Farhani M, Sahimi M, Asphalt flocculation and deposition: I. the onset of precipitation. AIChE Journal. 1996; 42:10-22.
8. Sheu E Y. Petroleum asphaltene properties, characterization, and issues. Energy & Fuels. 2002; 16:74-82.
9. Mullins O C. The modified Yen model. Energy & Fuels. 2010; 24:2179-2207.
10. Mullins O C, Sabbah H, Eyssautier J, Pomerantz A E, Barré L, Andrews A B, Ruiz-Morales Y, Mostowfi F, McFarlane R, Goual L, Lepkowicz R, Cooper T, Orbulescu J, Leblanc R M, Edwards J, Zare R N. Advances in asphaltene science and the Yen-Mullins model. Energy & Fuels. 2012; 26:3986-4003.
11. Adams J J. Asphaltene adsorption, a literature review. Energy & Fuels. 2014; 28:2831-2856.
12. Schuler B, Meyer G, Peña D, Mullins O C, Gross L. Unraveling the molecular structures of asphaltenes by atomic force microscopy. Journal of the American Chemical Society. 2015; 137:9870-9876.
13. Buckley J S. Microscopic investigation of the onset of asphaltene precipitation. Fuel Science and Technology International. 1996; 14:55-74.
14. Goual L, Sedghi M, Mostowfi F, McFarlane R, Pomerantz A E, Saraji S, Mullins O C. Cluster of asphaltene nanoaggregates by DC conductivity and centrifugation. Energy & Fuels. 2014; 28:5002-5013.
15. Goual L, Sedghi M, Zeng H, Mostowfi F, McFarlane R, Mullins O C. On the formation and properties of asphaltene nanoaggregates and clusters by DC-conductivity and centrifugation. Fuel. 2011; 90:2480-2490.
16. Mannistu K D, Yarranton H W, Masliyah J H. Solubility modeling of asphaltenes in organic solvents. Energy & Fuels. 1997; 11:615-622.
17. Alboudwarej H, Akbarzadeh K, Beck J, Svrcek W Y, Yarranton H W. Regular solution model for asphaltene precipitation from bitumens and solvents. AIChE Journal. 2003; 49:2948-2956.
18. Nikooyeh K, Shaw J M. On the applicability of the regular solution theory to asphaltene+diluent mixtures. Energy & Fuels. 2012; 26:576-585.
19. Victorov A I, Firoozabadi A. Thermodynamic micellizatin model of asphaltene precipitation from petroleum fluids. AIChE Journal. 1996; 42:1753-1764.
20. Tharanivasan A K, Yarranton H W, Taylor S D. Application of a regular solution-based model to asphaltene precipitation from live oils. Energy & Fuels. 2011;25:528-538.

21. Wu J, Prausnitz J M, Firoozabadi A. Molecular-thermodynamic framework for asphaltene-oil equilibria. AIChE Journal. 1998; 44:1188-1199.
22. Chapman W G, Gubbins K E, Jackson G, Radosz M. SAFT: equation-of-state solution model for associating fluids. Fluid Phase Equilibria. 1989; 52:31-38.
23. Wu J, Prausnitz J M, Firoozabadi A, Molecular thermodynamics of asphaltene precipitation in reservoir fluids. AIChE Journal. 2000; 46:197-209.
24. Vargas F M, Gonzalez D L, Hirasaki G J, Chapman W G. Modeling asphaltene phase behavior in crude oil systems using the perturbed chain form of the statistical associating fluid theory (PC-SAFT) equation of state. Energy & Fuels. 2009; 23:1140-1146.
25. Gross J, Sadowski G. Perturbed-chain SAFT: an equation of state based on a perturbation theory for chain molecules. Industrial & Engineering Chemistry Research. 2001; 40:1244-1260.
26. Mullins O C, Seifert D J, Zuo J Y, Zeybek M. Clusters of asphaltene nanoaggregates observed in oilfield reservoirs. Energy & Fuels. 2013; 27:1752-1761.
27. Zuo J Y, Mullins O C, Freed D, Elshahawi H, Dong C, Seifert D J. Advances in the Flory-Huggins-Zuo equation of state for asphaltene gradients and formation evaluation. Energy & Fuels. 2013; 27:1722-1735.
28. Rane J P, Harbottle D, Pauchard V, Couzis A, Banerjee S. Adsorption kinetics of asphaltenes at the oil-water interface and nanoaggregation in the bulk. Langmuir. 2012; 28:9986-9995.
29. Rane J P, Pauchard V, Couzis A, Banerjee S. Interfacial rheology of asphaltenes at oil-water interfaces and interpretation of the equation of state. Langmuir. 2013; 29:4750-4759.
30. Fredenslund A, Jones R L, Prausnitz J M. Group-contribution estimation of activity coefficients in nonideal liquid mixtures. AIChE Journal. 1975; 21:1086-1099.
31. Sayegh S G, Vera J H. Lattice-model expressions for the combinatotial entropy of liquid mixtures: a critical discussion. The Chemical Engineering Journal. 1980; 19:1-10.
32. Bondi A. Physical properties of molecular crystals, liquids and glasses. New York: John Wiley & Sons, Inc. 1968.
33. Abrams D S, Prausnitz J M. Statistical thermodynamics of liquid mixtures: a new expression for the excess Gibbs energy of partly or completely miscible systems. AIChE Journal. 1975; 21:116-128.
34. Hansen H K, Rasmussen P, Fredenslund A, Schiller M, Gmehling J. Vapor-liquid equilibria by UNIFAC group contribution. 5. revision and extension. Industrial & Engineering Chemistry Research. 1991; 30:2352-2355.
35. Tanveer S, Hao Y, Chen C-C. Introduction to solid-fluid equilibrium modeling. Chemical Engineering Progress. 2014; 110:37-47.
36. Wiehe I A, Yarranton H W, Akbarzadeh K, Rahimi P M, Teclemariam A. The paradox of asphaltene precipitation with normal paraffins. Energy & Fuels. 2005; 19:1261-1267.
37. Gómez-Álvarez P, Romani L, González-Salgado D. Association effects in pure methanol via Monte Carlo simulations. I. structure. Journal of Chemical Physics. 2013; 138:44509-44513.
38. Hermida-Ramón J M, Rios M A. The energy of interaction between two acetone molecules: a potential function constructed from ab Initio data. The Journal of Physical Chemistry A. 1998; 102:2594-2602.

What is claimed is:

1. A computerized method for thermodynamic modeling of asphaltene precipitation and treating a wellbore, pipeline, or downstream unit comprising: calculating a Gibbs free energy for a transition between asphaltene molecules in solution into a model crystalline asphaltene nanoaggregates or asphaltene nanocrystals using a computer using the formula:

$$\Delta G_{cryst} = -\Delta G_{fus} = RT \ln K_{sp} \quad (1)$$

where R is ideal gas constant, T is a system temperature, $\Delta G_{fus}$ is Gibbs free energy of fusion and Ksp is a solubility product constant of model asphaltene nanocrystals:

calculating a Gibbs free energy for a transition between asphaltene nanoaggregates or nanocrystals redissolving into colloidal asphaltene nanoaggregates using the computer using the formula:

$$\Delta G_{colloid} \cong RT \ln \gamma_{nano}^{\infty} \quad (2)$$

where $\gamma_{nano}^{\infty}$ is an "infinite dilution activity coefficient" of the asphaltene nanoaggregates in solution;

predicting asphaltene solubility in a solvent from the sum of (1) and (2)

$$\Delta G_{agg} = \Delta G_{cryst} + \Delta G_{colloid} = RT[\ln K_{sp} + \ln \gamma_{nano}^{\infty}] \quad (3), \text{ and}$$

calculating an equivalent solubility product constant for an asphaltene nanoaggregate formation process, $K_{sp}^{agg}$, from a change of Gibbs free energy:

$$\ln K_{sp}^{agg} = \frac{\Delta G_{agg}}{RT} = \ln x_{asp}^{agg} + \ln \gamma_{asp}^{agg} \quad (4)$$

where $X_{asp}$ and $\gamma_{asp}$ are a mole fraction and an activity coefficient of asphaltene molecule in solution, respectively, and wherein the predicted asphaltene solubility is displayed on an output device communicably coupled to the computer; and changing a solvent composition of an asphaltene based on the predicted asphaltene solubility in the solvent; and treating the wellbore, pipeline, or downstream unit operations with the solvent to prevent fouling and provide flow assurance for crude oil pipeline network or for petroleum blend.

2. The method of claim 1, wherein calculating the transition between asphaltene molecules in solution into the model crystalline asphaltene nanoaggregates or asphaltene nanocrystals is defined further as calculating the transition between

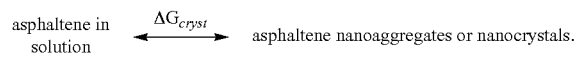

3. The method of claim 1, further comprising obtaining a downhole sample to determine an amount and type of asphaltene molecules in a formation, and calculating an amount of a solvent for injection into a formation to prevent formation damage and plugging of a well bore, or correcting formation damage and un-plugging of the well bore.

4. A method for preventing asphaltene fouling of a wellbore, pipeline, downstream unit operations, to provide flow assurance for crude oil pipeline network, or for petroleum crude blending with a solvent that prevents asphaltene precipitation or that redissolves precipitated asphaltenes based on a predictive thermodynamic model comprising:

calculating a Gibbs free energy for a transition between asphaltene molecules in solution into a model crystalline asphaltene nanoaggregates or asphaltene nanocrystals using the formula:

$$\Delta G_{cryst} = -\Delta G_{fus} = RT \ln K_{sp} \quad (1)$$

where R is ideal gas constant, T is a system temperature, $\Delta G_{fus}$ is Gibbs free energy of fusion and Ksp is a solubility product constant of model asphaltene nanocrystals;

calculating a Gibbs free energy for a transition between asphaltene nanoaggregates or nanocrystals redissolving into colloidal asphaltene nanoaggregates using the formula:

$$\Delta G_{colloid} \approx RT \ln \gamma_{nano}^{\infty} \quad (2)$$

where $\gamma_{nano}^{\infty}$ is an "infinite dilution activity coefficient" of the asphaltene nanoaggregates in solution;

predicting asphaltene solubility using different solvents from the sum of (1) and (2)

$$\Delta G_{agg} = \Delta G_{cryst} + \Delta G_{colloid} = RT[\ln K_{sp} + \ln \gamma_{nano}^{\infty}] \quad (3), \text{ and}$$

calculating an equivalent solubility product constant for an asphaltene nanoaggregate formation process, $K_{sp}^{agg}$, from a change of Gibbs free energy:

$$\ln K_{sp}^{agg} = \frac{\Delta G_{agg}}{RT} = \ln x_{asp}^{agg} + \ln \gamma_{asp}^{agg} \quad (4)$$

where $x_{asp}$ and $\gamma_{asp}$ are a mole fraction and an activity coefficient of asphaltene molecule in solution, respectively;

selecting a solvent based on the predicted asphaltene solubility and the activity coefficient of asphaltene molecule in solution;

calculating and adding an amount of the solvent sufficient to prevent fouling of the wellbore, pipeline, downstream unit operations, to provide flow assurance for crude oil pipeline network, or for petroleum crude blending; and treating the wellbore, pipeline, downstream unit operations with the solvent to preventing asphaltene fouling.

5. The method of claim 4, wherein calculating a transition between asphaltene molecules in solution into the model crystalline asphaltene nanoaggregates or asphaltene nanocrystals is defined further as calculating the transition between

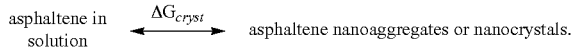

6. The method of claim 4, wherein calculating an amount of a solvent identified is added to an asphaltene to prevent asphaltene nanoaggregate or asphaltene nanocrystal formation, or that solubilizes asphaltene nanoaggregate or asphaltene nanocrystal into colloidal asphaltene nanoaggregates to prevent fouling of the wellbore, pipeline, downstream unit operations, to provide flow assurance for crude oil pipeline network, or for petroleum crude blending.

7. The method of claim 4, further comprising obtaining a downhole sample to determined an amount and type of asphaltene molecules in a formation, and calculating an amount of a solvent for injection into a formation to prevent formation damage and plugging of the well bore, or correcting formation damage and un-plugging of the well bore.

8. A non-transitory computer readable medium encoded with a computer program for execution by a processor for optimizing a predictive thermodynamic model for asphaltene molecules for treating a wellbore, pipeline, downstream unit operation, the computer program comprising:

a code segment for calculating a Gibbs free energy for a transition between asphaltene molecules in solution into a model crystalline asphaltene nanoaggregates or asphaltene nanocrystals using the formula:

$$\Delta G_{cryst} = -\Delta G_{fus} = RT \ln K_{sp} \quad (1)$$

where R is ideal gas constant, T is a system temperature, $\Delta G_{fus}$ is Gibbs free energy of fusion and Ksp is a solubility product constant of model asphaltene nanocrystals:

calculating a Gibbs free energy for a transition between asphaltene nanoaggregates or nanocrystals redissolving into colloidal asphaltene nanoaggregates using the formula:

$$\Delta G_{colloid} \approx RT \ln \gamma_{nano}^{\infty} \quad (2)$$

where $\gamma_{nano}^{\infty}$ is an "infinite dilution activity coefficient" of the asphaltene nanoaggregates in solution;

a code segment for predicting asphaltene solubility in a solvent from the sum of (1) and (2)

$$\Delta G_{agg} = \Delta G_{cryst} + \Delta G_{colloid} = RT[\ln K_{sp} + \ln \gamma_{nano}^{\infty}] \quad (3), \text{ and}$$

calculating an equivalent solubility product constant for an asphaltene nanoaggregate formation process, $K_{sp}^{agg}$, from a change of Gibbs free energy:

$$\ln K_{sp}^{agg} = \frac{\Delta G_{agg}}{RT} = \ln x_{asp}^{agg} + \ln \gamma_{asp}^{agg} \quad (4)$$

where $X_{asp}$ and $\gamma_{asp}$ are a mole fraction and an activity coefficient of asphaltene molecule in solution, respectively; and wherein the predicted asphaltene solubility is displayed on an output device communicably to the computer;

adding an amount of the solvent to an asphaltene; and treating the wellbore, pipeline, or downstream unit operations with the solvent to preventing fouling and provide flow assurance for crude oil pipeline network or for petroleum blend.

9. The medium of claim 8, further comprising a code segment for calculating a transition between asphaltene molecules in solution into model crystalline asphaltene nanoaggregates or asphaltene nanocrystals is defined further as calculating a transition between

10. The medium of claim 8, wherein the processor calculates an amount of a solvent identified that prevents asphaltene nanoaggregate or asphaltene nanocrystal formation, or that solubilizes asphaltene nanoaggregate or asphaltene nanocrystal into colloidal asphaltene nanoaggregates.

11. An apparatus for optimizing a thermodynamic model of solubility of asphaltenes for treating a wellbore, pipeline, or downstream unit operation comprising:

a processor;
a memory communicably coupled to the processor;
an output device communicably coupled to the processor; and
a non-transitory computer readable medium encoded with a computer program for execution by the processor that causes the processor to:
calculate a Gibbs free energy for the transition between asphaltene molecules in solution into a model crystalline asphaltene nanoaggregates or asphaltene nanocrystals using a computer using the formula:

$$\Delta G_{cryst} = -\Delta G_{fus} = RT \ln K_{sp} \quad (1)$$

where R is ideal gas constant, T is a system temperature, $\Delta G_{fus}$ is Gibbs free energy of fusion and Ksp is a solubility product constant of model asphaltene nanocrystals:
and to calculate a Gibbs free energy for a transition between asphaltene nanoaggregates or nanocrystals redissolving into colloidal asphaltene nanoaggregates using the formula:

$$\Delta G_{colloid} \approx RT \ln \gamma_{nano}^{\infty} \quad (2)$$

where $\gamma_{nano}^{\infty}$ is an "infinite dilution activity coefficient" of the asphaltene nanoaggregates in solution;
predicting asphaltene solubility in a solvent from the sum of (1) and (2)

$$\Delta G_{agg} = \Delta G_{cryst} + \Delta G_{colloid} = RT[\ln K_{sp} + \ln \gamma_{nano}^{\infty}] \quad (3), \text{ and}$$

calculating an equivalent solubility product constant for an asphaltene nanoaggregate formation process, $K_{sp}^{agg}$, from a change of Gibbs free energy:

$$\ln K_{sp}^{agg} = \frac{\Delta G_{agg}}{RT} = \ln x_{asp}^{agg} + \ln \gamma_{asp}^{agg} \quad (4)$$

where $X_{asp}$ and $\gamma_{asp}$ are a mole fraction and an activity coefficient of asphaltene molecule in solution, respectively; and wherein the processor outputs solubility data for the asphaltenes in one or more solvents,
adding an amount of the solvent to asphaltenes; and
treating the wellbore, pipeline, or downstream unit operations with the solvent to preventing fouling and provide flow assurance for crude oil pipeline network or for petroleum blend.

12. The apparatus of claim 11, wherein the processor calculates a transition between asphaltene molecules in solution into model crystalline asphaltene nanoaggregates or asphaltene nanocrystals is defined further as calculating a transition between

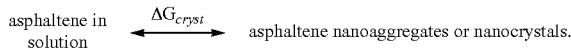

13. The apparatus of claim 11, wherein the processor calculates an amount of a solvent identified to be added to an asphaltene comprising liquid or solid that prevents asphaltene nanoaggregate or asphaltene nanocrystal formation, or that solubilizes asphaltene nanoaggregate or asphaltene nanocrystal into colloidal asphaltene nanoaggregates to prevent fouling of the wellbore, pipeline, downstream unit operations, to provide flow assurance for crude oil pipeline network, or for petroleum crude blending.

14. The apparatus of claim 11, wherein the processor calculates an amount of a solvent to introduce into a formation to prevent formation damage and plugging of a well bore, or correcting formation damage and un-plugging of the well bore.

15. A non-transitory computer readable medium encoded with a computer program for execution by a processor for generating a thermodynamic model of solubility of asphaltenes for treating a wellbore, pipeline, or downstream unit operation, the computer program comprising:
calculating a Gibbs free energy for a transition between asphaltene molecules in solution into model crystalline asphaltene nanoaggregates or asphaltene nanocrystals using a computer using the formula:

$$\Delta G_{cryst} = -\Delta G_{fus} = RT \ln K_{sp} \quad (1)$$

where R is ideal gas constant, T is a system temperature, $\Delta G_{fus}$ is Gibbs free energy of fusion and Ksp is a solubility product constant of model asphaltene nanocrystals;
calculating a Gibbs free energy for a transition between asphaltene nanoaggregates or nanocrystals redissolving into colloidal asphaltene nanoaggregates using the computer using the formula:

$$\Delta G_{colloid} \approx RT \ln \gamma_{nano}^{\infty} \quad (2)$$

where $\gamma_{nano}^{\infty}$ is a "infinite dilution activity coefficient" of the asphaltene nanoaggregates in solution; and
predicting asphaltene solubility using different solvents from the sum of (1) and (2)

$$\Delta G_{agg} = \Delta G_{cryst} + \Delta G_{colloid} = RT[\ln K_{sp} + \ln \gamma_{nano}^{\infty}] \quad (3), \text{ and}$$

calculating an equivalent solubility product constant for an asphaltene nanoaggregate formation process, $K_{sp}^{agg}$, from a change of Gibbs free energy:

$$\ln K_{sp}^{agg} = \frac{\Delta G_{agg}}{RT} = \ln x_{asp}^{agg} + \ln \gamma_{asp}^{agg} \quad (4)$$

where $x_{asp}$ and $\gamma_{asp}$ are a mole fraction and an activity coefficient of asphaltene molecule in solution, respectively;
selecting a solvent based on the predicted solubility in a predictive thermodynamic model;
calculating and adding an amount of the solvent sufficient to prevent asphaltene precipitation, or to redissolve precipitated asphaltene, wherein the solvent prevents fouling of the wellbore, the pipeline, the downstream unit operations, provides flow assurance for the crude oil pipeline network, or for petroleum crude blending; and
treating the wellbore, pipeline, or downstream unit operations with the solvent.

16. The medium of claim 15, further comprising a code segment for calculating a transition between asphaltene molecules in solution into model crystalline asphaltene nanoaggregates or asphaltene nanocrystals is defined further as calculating a transition between

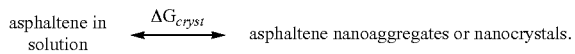

17. The medium of claim 15, wherein the processor calculates an amount of a solvent identified to be added to an asphaltene comprising liquid or solid that prevents asphaltene nanoaggregate or asphaltene nanocrystal formation, or that solubilizes asphaltene nanoaggregate or asphaltene nanocrystal into colloidal asphaltene nanoaggregates to prevent fouling of the wellbore, pipeline, downstream unit operations, to provide flow assurance for crude oil pipeline network, or for petroleum crude blending.

\* \* \* \* \*